US010557855B2

(12) United States Patent
Korgel et al.

(10) Patent No.: US 10,557,855 B2
(45) Date of Patent: Feb. 11, 2020

(54) SILICON QUANTUM DOT OPTICAL PROBES

(71) Applicants: BOARD OF REGENTS, THE UNIVERSITY OF TEXAS SYSTEM, Austin, TX (US); Alma Mater Studiorum—Università di Bologna, Bologna (IT)

(72) Inventors: Brian A. Korgel, Round Rock, TX (US); Yixuan Yu, Austin, TX (US); Paola Ceroni, Bagnara di Romagna (IT); Giacomo Bergamini, Bologna (IT); Mirko Locritani, Taranto (IT)

(73) Assignees: Board of Regents, The University of Texas System, Austin, TX (US); Alma Mater Studiorum—Universita di Bologna, Bologna (IT)

( * ) Notice: Subject to any disclaimer, the term of this patent is extended or adjusted under 35 U.S.C. 154(b) by 81 days.

(21) Appl. No.: 15/504,909

(22) PCT Filed: Aug. 19, 2015

(86) PCT No.: PCT/US2015/045825
§ 371 (c)(1),
(2) Date: Feb. 17, 2017

(87) PCT Pub. No.: WO2016/028855
PCT Pub. Date: Feb. 25, 2016

(65) Prior Publication Data
US 2017/0269097 A1  Sep. 21, 2017

Related U.S. Application Data

(60) Provisional application No. 62/165,869, filed on May 22, 2015, provisional application No. 62/039,277, filed on Aug. 19, 2014.

(51) Int. Cl.
*G01N 33/58* (2006.01)
*C09K 11/06* (2006.01)
(Continued)

(52) U.S. Cl.
CPC ............ *G01N 33/588* (2013.01); *C09K 11/06* (2013.01); *G01N 33/582* (2013.01); *B82Y 15/00* (2013.01);
(Continued)

(58) Field of Classification Search
None
See application file for complete search history.

(56) References Cited

U.S. PATENT DOCUMENTS 4,895,936 A * 1/1990 Talebian ............. C07F 15/0093
536/121
6,500,622 B2  12/2002 Bruchez et al.
(Continued)

FOREIGN PATENT DOCUMENTS

WO  2012075087 A2  6/2012
WO  2014206918 A1  12/2014

OTHER PUBLICATIONS

Communication Pursuant to Rule 164(1) EPC, issued in European Application No. 15833017.5, dated Mar. 1, 2018, 21 pages.
(Continued)

*Primary Examiner* — Robert T. Crow
(74) *Attorney, Agent, or Firm* — Kilpatrick Townsend & Stockton LLP

(57) ABSTRACT

Systems comprising a nanocrystal and a luminescent chromophore are disclosed herein. The luminescent chromophore can emit energy having a first wavelength. The luminescent chromophore is configured to transfer the emitted energy having a first wavelength to the nanocrystal. The luminescent chromophore can be linked to the nanocrystal
(Continued)

via a covalent bond. Absorption of the energy having first wavelength by the nanocrystal can activate the nanocrystal and result in an increase in quantum yield. In some embodiments, the nanocrystal can include silicon, germanium, carbon, or combinations thereof. In some examples, the luminescent chromophore can be pyrene. The luminescent chromophore and the silicon containing nanocrystal can be in a ratio of about 1:1 to 100:1 in the nanocrystal system. Methods of making and using the system are also disclosed.

35 Claims, 18 Drawing Sheets

(51) Int. Cl.
  B82Y 15/00    (2011.01)
  B82Y 20/00    (2011.01)
  B82Y 40/00    (2011.01)
(52) U.S. Cl.
  CPC ............. B82Y 20/00 (2013.01); B82Y 40/00 (2013.01); C09K 2211/1011 (2013.01); Y10S 977/774 (2013.01); Y10S 977/896 (2013.01); Y10S 977/92 (2013.01)

(56) References Cited

U.S. PATENT DOCUMENTS

| | | | |
|---|---|---|---|
| 2004/0072373 A1* | 4/2004 | Lin | B82Y 15/00 436/526 |
| 2004/0171827 A1* | 9/2004 | Peng | C09B 69/008 540/145 |
| 2005/0148100 A1* | 7/2005 | Su | C12Q 1/6816 436/523 |
| 2005/0266456 A1* | 12/2005 | Williams | C12Q 1/6869 435/6.11 |
| 2008/0213189 A1 | 9/2008 | Lee et al. | |
| 2011/0144718 A1* | 6/2011 | Diwan | A61K 9/0085 607/50 |
| 2011/0256549 A1* | 10/2011 | Gaylord | C08G 61/02 435/7.1 |
| 2012/0029155 A1 | 2/2012 | Gaylord et al. | |
| 2013/0287735 A1* | 10/2013 | Cosgriff-Hernandez | A61K 9/107 424/93.1 |
| 2014/0071517 A1 | 3/2014 | Schut et al. | |

OTHER PUBLICATIONS

Xu Z: "Synthesis, characterization and fictionalization of silicon nanoparticle based hybrid nanomaterials for photovoltaic and biological applications", Thesis, University School of Science and Engineering, Chapter 4, pp. 129-177, 2001.
Cheng-Lan Lin, et al., "Silica-Titania-Based Organic-Inorganic Hybrid Materials for Photovoltaic Applications", Chem. Mater., 18 (17), pp. 4157-4162, 2006.
Deng S.S., et al., "Higher fullerene-coupled porous silicon systems with blue emission", Acta Materialia 52(7), pp. 1953-1957, 2004.
Zhang D., et al., "Preparation of hybrid mesoporous silica luminescent nanoparticles with lanthanide(III) complexes and their exhibition of white emission", Dalton Transactions: The International Journal for Inorganic, Organometallic and Bioinorganic Chemistry 40(36), pp. 9313-9319, 2011.
International Preliminary Report on Patentability issued in Application No. PCT/US15/45825, dated Mar. 2, 2017.
International Search Report and Written Opinion issued in Application No. PCT/US15/45825, dated Nov. 24, 2015.
Accorsi et al., "Taking Advantage of the Electronic Excited States of [60]-Fullerenes", Acc. Chem. Res. 33, 2000, 695-703.
Ann et al., "Stable aqueous dispersions of noncovalently functionalized graphene from graphite and their multifunctional high-performance applications", Nano Lett. 10, 2010, 4295-4301.
Barillaro et al., "Color tuning of light-emitting-diodes by modulating the concentration of red-emitting silicon nanocrystal phosphors", Appl. Phys. Lett. 104, 2014, 091102.
Bae, et al., "Electrochemistry and electrogenerated chemiluminescence of films of silicon nanoparticles in aqueous solution", Nanotechnology 17, 2006, 3791-3797.
Beljonne, et al., "Beyond Förster resonance energy transfer in biological and nanoscale systems.", J. Phys. Chem. B 113, 2009, 6583-6599.
Brus, et al., "Electronic Spectroscopy and Photophysics of Si Nanocrystals: Relationship to Bulk c-Si and Porous Si", J. Am. Chem. Soc.117 (10), 1995, 2915-2922.
Buriak, "Illuminating Silicon Surface Hydrosilylation: An Unexpected Plurality of Mechanisms", Chem. Mater. 26, 2014, 763-772.
Carvalho et al., "Charge Injection Rates in Hybrid Nanosilicon—Polythiophene Bulk Heterojunction Solar Cells" J. Phys. Chem. C 117, 2013, 110-115.
Chen et al., "Noncovalent Sidewall Functionalization of Single-Walled Carbon Nanotubes for Protein Immobilization", J. Am. Chem. Soc. 123, 2001, 3838-3839.
Chen et al., "Energy Transfer from Individual Semiconductor Nanocrystals to Graphene", ACS Nano 4, 2010, 2964-2968.
Crosby et al., "Measurement of photoluminescence quantum yields. Review", J. Phys. Chem. 75, 1971,991-1024.
Demas, et al., "Measurement of photoluminescence quantum yields. Review", 1971, 991-1024.
Ding, et al., "Electrochemistry and electrogenerated chemiluminescence from silicon nanocrystal quantum dots.", Science 296(5571), 2002, 1293-7.
Enghag, P. In Encyclopedia of the Elements: Technical Data—History—Processing—Applications; Wiley-VCH: Weinheim, 2004; p. 920.
Erogbogbo, et al., "Energy transfer from a dye donor to enhance the luminescence of silicon quantum dots", Nanoscale 4, 2012, 5163-5168.
Erogbogbo, et al., "In Vivo Targeted Cancer Imaging, Sentinel Lymph Node Mapping and Multi-Channel Imaging with Biocompatible Silicon Nanocrystals", ACS Nano 5, 2011, 413-423.
Gonzalez et al., "Detection of high-energy compounds using photoluminescent silicon nanocrystal paper based sensors", Nanoscale 6, 2014, 2608-2612.
Gu et al., "In vivo time-gated fluorescence imaging with biodegradable luminescent porous silicon nanoparticles", Nat. Commun. 4, 2013, 15 pages.
Guldi et al., "Excited-State Properties of $C_{60}$ Fullerene Derivatives", Acc. Chem. Res. 33, 2000, 695-703.
Ghosh et al., "Hybrid White Light Emitting Diode Based on Silicon Nanocrystals", Adv. Funct. Mater. 2014, 24, 7151-7160.
He et al., "One-Pot Microwave Synthesis of Water-Dispersible, Ultraphoto- and pH-Stable, and Highly Fluorescent Silicon Quantum Dots", J. Am. Chem. Soc. 2011, 133, 14192-14195.
Henderson, et al., "Colloidally stable silicon nanocrystals with near-infrared photoluminescence for biological fluorescence imaging", Small 5;7(17), 2011, 2507-16.
Herrmann et al., "Role of Structural Order and Excess Energy on Ultrafast Free Charge Generation in Hybrid Polythiophene/Si Photovoltaics Probed in Real Time by Near-Infrared Broadband Transient Absorption", J. Am. Chem. Soc. 133, 2011, 18220-18233.
Hessel, et al., "Hydrogen Silsesquioxane: A Molecular Precursor for Nanocrystalline Si-SiO$_2$ Composites and Freestanding Hydride-Surface-Terminated Silicon Nanoparticles", Chem. Mater. 18, 2006, 6139-6146.
Hessel, et al., "Alkyl Passivation and Amphiphilic Polymer Coating of Silicon Nanocrystals for Diagnostic Imaging", Small 6, 2010, 2026-2034.
Hessel, et al., "Synthesis of Ligand-Stabilized Silicon Nanocrystals with Size-Dependent Photoluminescence Spanning Visible to Near-Infrared Wavelengths", Chem. Mater. 24, 2012, 393-401.

(56) References Cited

OTHER PUBLICATIONS

Hodes, "When Small Is Different: Some Recent Advances in Concepts and Applications of Nanoscale Phenomena", Adv. Mater. 19, 2007, 639-655.

Hung et al., "A precise determination of the triplet energy of carbon (C60) by photoacoustic calorimetry", J. Phys. Chem. 95, 1991, 6073-6075.

Hwang et al., "Nonlinear Stern-Volmer Fluorescence Quenching of Pyrene by C60/70", Fuller. Sci. Technol. 7, 1999, 437-454.

Kelly et al., "Sol-gel precursors for group 14 nanocrystals", Chem. Commun. 46, 2010, 8704-8718.

Jeong, et al. "Core-Shell Structured Silicon Nanoparticles©$TiO_{2-x}$/ Carbon Mesoporous Microfiber Composite as a Safe and High-Performance Lithium-Ion Battery Anode", ACS Nano 8, 2014, 2977-2985.

Kang et al., "A polyoxometalate-assisted electrochemical method for silicon nanostructures preparation: from quantum dots to nanowires", J. Am. Chem. Soc. 2007, 129, 5326-5327.

Kim et al., "A Critical Size of Silicon Nano-Anodes for Lithium Rechargeable Batteries", Angew. Chem. Int. Ed. 2010, 49, 2146-2149.

Kovalev, et al., "Optical absorption cross sections of Si nanocrystals", Phys. Rev. B 2000, 61, 4485-4487.

Li, et al., "Process for Preparing Macroscopic Quantities of Brightly Photoluminescent Silicon Nanoparticles with Emission Spanning the Visible Spectrum", Langmuir 2003, 19, 8490-8496.

Liu, et al., "Assessing Clinical Prospects of Silicon Quantum Dots: Studies in Mice and Monkeys", ACS Nano 7(8), 2013, 7303-7310.

Liu, et al., "Photoinduced Electron Transfer and Enhancement of Photoconductivity in Silicon Nanoparticles/Perylene Diimide Composites in a Polymer Matrix", J. Phys. Chem. C 112(40), 2008, 15865-15869.

Locritani et al., "Silicon Nanocrystals Functionalized with Pyrene Units: Efficient Light-Harvesting Antennae with Bright Near-Infrared Emission", J. Phys. Chem. Lett. 5, 2014,3325-3329.

Maier-Flaig et al., "Multicolor Silicon Light-Emitting Diodes (SiLEDs)", Nano Lett. 13, 2013, 475-480.

Mangolini et al., "High-Yield Plasma Synthesis of Luminescent Silicon Nanocrystals", Nano Lett. 5, 2005, 655-659.

Mastronardi, et al., "Size-dependent absolute quantum yields for size-separated colloidally-stable silicon nanocrystals", Nano Lett. 12, 2012,337-342.

Mastronardi et al., "Small Silicon, Big Opportunities: The Development and Future of Colloidally-Stable Monodisperse Silicon Nanocrystals", Adv. Mater. 24, 2012, 5890-5898.

McVey, et al. "Solution synthesis, optical properties, and bioimaging applications of silicon nanocrystals", Acc Chem. Res., 47(10), 2014, 3045-54.

Medintz, et al., "Quantum dot-based resonance energy transfer and its growing application in biology", Phys. Chem. Chem. Phys. 11, 2009,17-45.

Miller, et al., "Ensemble Brightening and Enhanced Quantum Yield in Size-Purified Silicon Nanocrystals", ACS Nano 6, 2012, 7389-7396.

Nojiri et al., "Photoinduced Electron Transfer between $C_{60}/C_{70}$ and Zinc Tetraphenylporphyrin in Polar Solvents", J. Phys. Chem. A 102, 1998, 5215-5219.

Ortolani et al., "Folded Graphene Membranes: Mapping Curvature at the Nanoscale", Nano Lett. 12, 2012, 5207-5212.

Panthani et al., "Graphene-Supported High-Resolution TEM and STEM Imaging of Silicon Nanocrystals and their Capping Ligands", J. Phys. Chem. C 116, 2012, 22463-22468.

Park, et al., "Biodegradable luminescent porous silicon nanoparticles for in vivo applications", Nat. Mater. 8, 2009, 331-336.

Rio et al., "A fullerene core to probe dendritic shield effects", Tetrahedron 2003, 59, 3833-3844.

Rosso-Vasic, et al., "Efficient Energy Transfer between Silicon Nanoparticles and a Ru-Polypyridine Complex", J. Phys. Chem. C 2009, 113 (6), 2235-2240.

Rosso-Vasic, et al., "Alkyl-Functionalized Oxide-Free Silicon Nanoparticles: Synthesis and Optical Properties", Small 2008, 4, 1835-1841.

Schlierf et al., "Nanoscale insight into the exfoliation mechanism of graphene with organic dyes: effect of charge, dipole and molecular structure", Nanoscale 2013, 5, 4205-4216.

Semonin, et al., "Absolute Photoluminescence Quantum Yields of IR-26 Dye, PbS, and PbSe Quantum Dots", J. Phys. Chem. Lett. 1(16), 2010, 2445-2450.

Sension et al., "Transient absorption studies of carbon (C60) in solution", J. Phys. Chem. 95, 1991, 6075-6078.

Shiohara, et al., "Sized controlled synthesis, purification, and cell studies with silicon quantum dots", Nanoscale 3, 2011,3364-3370.

Sommer, et al., "Ultrafast Excitation Energy Transfer in Vinylpyridine Terminated Silicon Quantum Dots", J. Phys. Chem. C. 115(46), 2011, 22781-22788.

Suzuki et al., "Reevaluation of absolute luminescence quantum yields of standard solutions using a spectrometer with an integrating sphere and a back-thinned CCD detector", Phys. Chem. Chem. Phys. 11, 2009, 9850-9860.

Veinot, et al., "Synthesis, surface functionalization, and properties of freestanding silicon nanocrystals", Chem. Commun. 2006, 4160-4168.

Warner et al., "Water-soluble photoluminescent silicon quantum dots", Angew. Chem. Int. Ed. 44, 2005, 4550-4554.

Wurth, et al., "Integrating Sphere Setup for the Traceable Measurement of Absolute Photoluminescence Quantum Yields in the Near Infrared", Anal. Chem. 84, 2012, 1345-1352.

Wurth, et al., "Relative and absolute determination of fluorescence quantum yields of transparent samples", Nature Prot. 8, 2013, 1535-1550.

Yi et al., "A Label-Free Silicon Quantum Dots-Based Photoluminescence Sensor for Ultrasensitive Detection of Pesticides", Anal. Chem. 85, 2013, 11464-11470.

Extended European Search Report dated Jun. 6, 2018, from related EP Application No. 15833017.5, 17 pages.

* cited by examiner

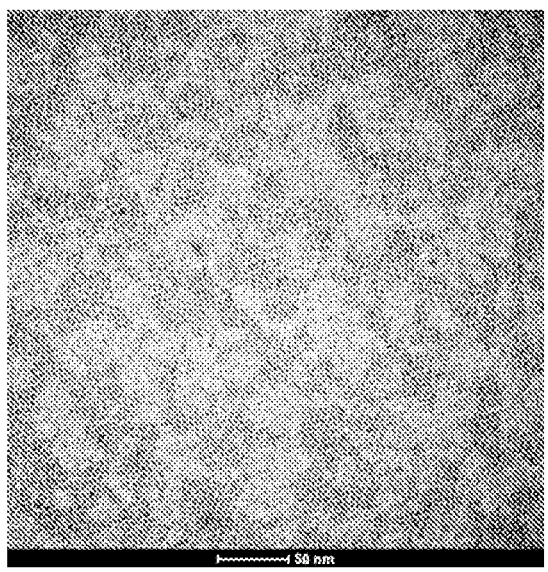
FIG. 2A　　　　　　　　　　　　　　　FIG. 2B
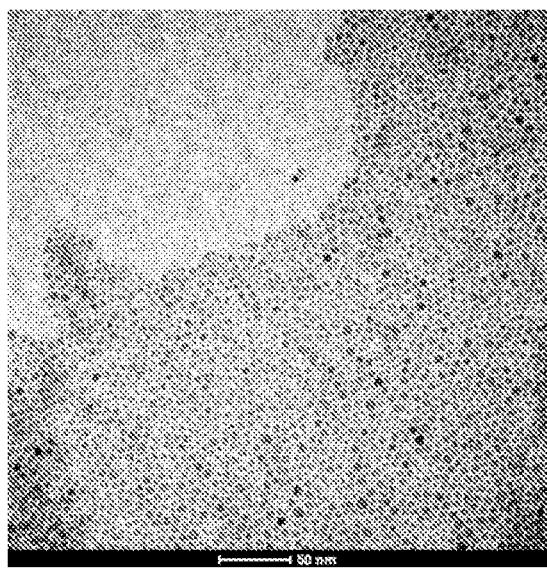
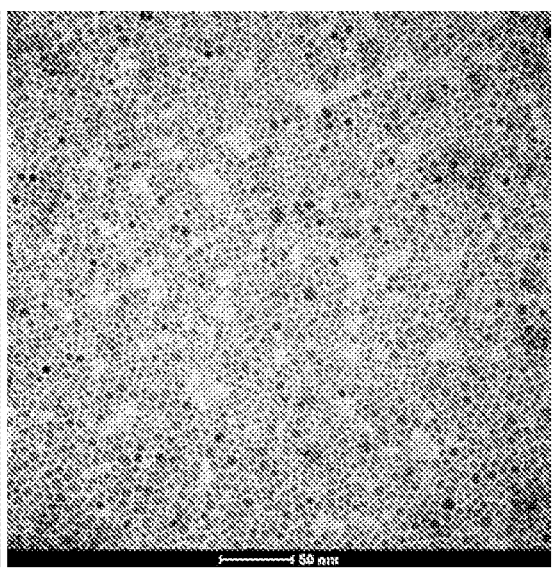
FIG. 2C　　　　　　　　　　　　　　　FIG. 2D

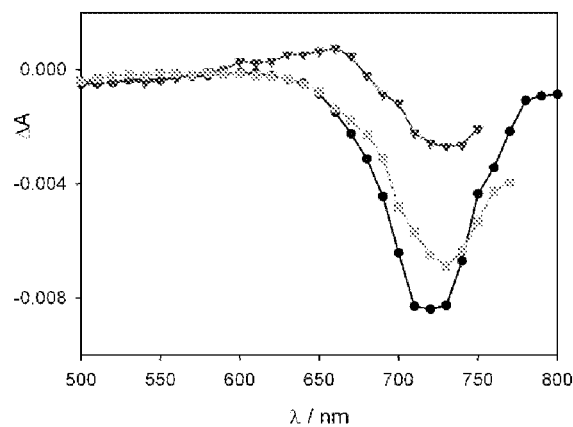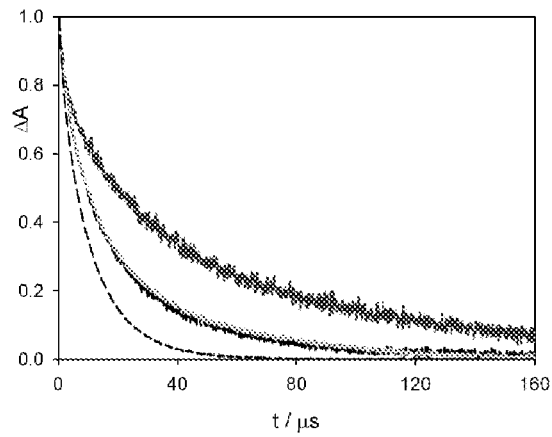
FIG. 23A                    FIG. 23B
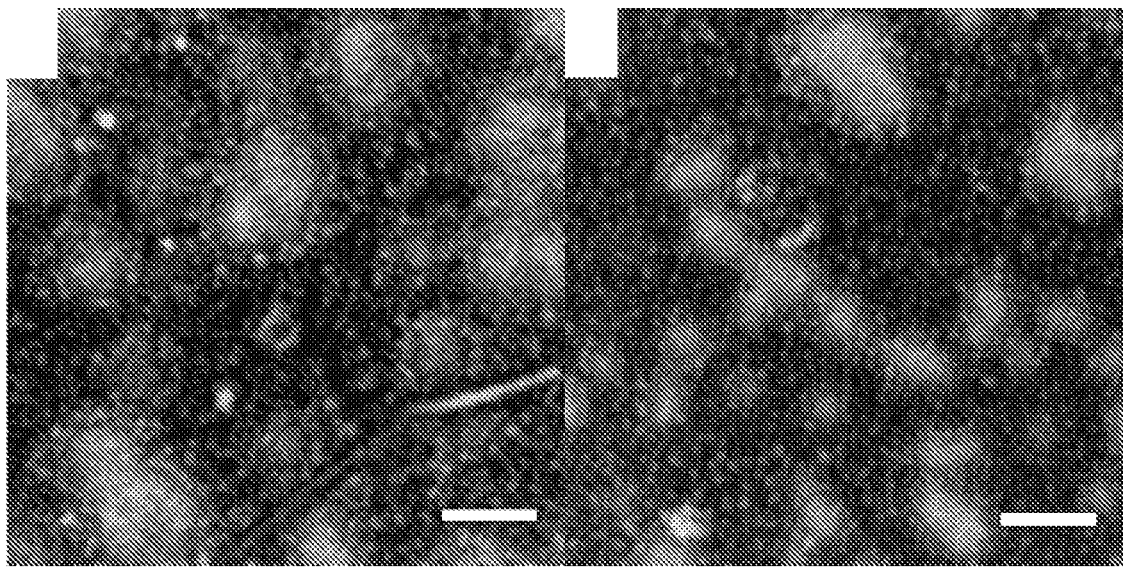
FIG. 24A                    FIG. 24B

SILICON QUANTUM DOT OPTICAL PROBES

ACKNOWLEDGEMENTS

This invention was made with Government support under grant CHE1308813 awarded by the National Science Foundation. The Government has certain rights in the invention.

The work leading to this invention has received funding from the European Research Council Executive Agency under the European Union's Seventh Framework Program (FP7/2007-2013)/ERC grant agreement no. 278912.

FIELD

The disclosed subject matter relates generally to nanocrystals, more particularly to nanocrystals conjugated to a luminescent chromophore.

BACKGROUND

Silicon is an extraordinarily useful semiconductor, employed in integrated circuits, solar cells and photodetectors; however, it exhibits no significant luminescence at room temperature because of its indirect band gap. Silicon nanocrystals (SiNCs) in the quantum size range (2-12 nm) can be efficient light emitters, with emission wavelength that can be tuned by size from the near-infrared (NIR) into the visible range (McVey, et al. *Acc. Chem. Res.* 2014, 47:3045-3051; Mastronardi, et al. *Adv. Mater.* 2012, 24:5890-5898). Moreover, silicon nanocrystals, being composed of a single, elementally nontoxic material that is potentially biodegradable, earth abundant, ecologically safe, and known to be metabolized, may satisfy the above criteria for nanocrystals rapid progression to the clinic. The indirect band gap of silicon, however, still makes light absorption relatively weak compared to nanocrystals of direct band gap semiconductors, especially at wavelengths near the absorption edge. This leads to a large apparent Stokes shift between excitation and emission wavelengths of nanocrystals.

Ding, et al. (*J. Science,* 2002, 296:1293-1297) discloses induced silicon nanocrystal luminescence by electrochemical charge injection. Liu, et al. (*J. Phys. Chem. C,* 2008, 112:15865-15869) discloses energy transfer between a perylene diimide derivative and silicon nanocrystals embedded in polymer (PMMA). Rosso-Vasic, et al. (*J. Phys. Chem. C,* 2009, 113:2235-2240) discloses energy transfer between a Ru-based dye and blue-emitting silicon nanocrystal. Sommer, et al. (*J. Phys. Chem. C,* 2011, 115:22781-22788) discloses fast energy transfer (270 fs to 3 ns) from vinylpyridine ligands to silicon nanocrystals. Erogbogbo, et al. (*Nanoscale,* 2012, 4: 5163-5168) discloses enhancement in brightness of silicon nanocrystals by an anthracene-based dye in the hydrophobic core of micelles due to energy transfer.

There is still a need to enhance the optical absorption of nanocrystals. There is still a need to enhance the optical absorption of silicon nanocrystals while retaining their emissive properties. There is still a need to create significantly brighter silicon nanocrystals. In accordance, the present disclosure addresses these needs.

SUMMARY

Systems comprising a nanocrystal and a luminescent chromophore are disclosed herein. The luminescent chromophore can emit energy having a first wavelength. Excitation of the luminescent chromophore by electromagnetic radiation having a second wavelength, such as by visible radiation, can result in emission of energy having a first wavelength. The luminescent chromophore is configured to transfer the emitted energy having a first wavelength to the nanocrystal. For example, the luminescent chromophore can be linked to the nanocrystal via a covalent bond. Absorption of the energy having first wavelength by the nanocrystal can activate the nanocrystal and result in an increase in quantum yield.

In some embodiments, the nanocrystal can include a semiconductor that comprises a wide band gap. For example, the nanocrystal can be a Group IV nanocrystal. Examples or suitable nanocrystal can include silicon, germanium, carbon, or combinations thereof. The systems can also contain a luminescent chromophore useful for transferring their emitted energy to the nanocrystal. In some examples, the emission spectrum of the luminescent chromophore can be matched to the absorption spectrum of the nanocrystal. In other examples, the emission spectrum of the luminescent chromophore can be partially overlapped with the absorption spectrum of the nanocrystal. In even other examples, the emission spectrum of the luminescent chromophore does not overlap with the absorption spectra of the nanocrystal. The luminescent chromophore can emit energy having a first wavelength. In some embodiments, the luminescent chromophore can emit energy having a first wavelength in the visible or near infrared portions of the electromagnetic spectrum. In some examples, the luminescent chromophore can be pyrene. The luminescent chromophore and the silicon containing nanocrystal can be in a ratio of about 1:1 to 100:1 in the nanocrystal system. The systems described herein can exhibit a quantum yield. In some embodiments, the system can exhibit an increase in photoluminescence quantum yield of at least double that of the nanocrystal without the luminescent chromophore. In some embodiments, a greater amount of energy having said second wavelength can be absorbed by the system than the silicon containing nanocrystal. The energy of said second wavelength can be transferred with at least 60% efficiency from the luminescent chromophore to the silicon containing nanocrystal. In some embodiments, the system can exhibit a greater intensity of brightness than the silicon containing nanocrystal only.

The specificity of the disclosed systems can be increased by conjugation of the system with a target recognition moiety, which specifically binds to a component on the surface of, for example, a target cell or tissue. Suitable target recognition moieties include, but are not limited to, a receptor, ligand, polynucleotide, peptide, polynucleotide binding agent, antigen, antibody, or combinations thereof.

The systems disclosed herein can be prepared as or formulated into a composition. In some examples, the systems can be formulated into a pharmaceutical composition. Methods of making the systems disclosed herein are also provided. The method can include dispersing the silicon containing nanocrystal in the solution of a luminescent chromophore and heating the dispersion of silicon containing nanocrystal in the solution of the luminescent chromophore.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments of the disclosure and together with the description, serve to explain the principles of the disclosure.

FIGS. 2A-2D show TEM images of 2.6 nm diameter SiNC-Py (FIG. 2A), 2.6 nm diameter SiNC (FIG. 2B), 5.0 nm diameter SiNC-Py (FIG. 2C), and 5.0 nm diameter SiNC (FIG. 2D).

FIG. 11A is a Stern-Volmer plot reporting the lifetimes of the Si core emission at 700 nm of SiNC($C_{11}$)Py. $\lambda_{ex}$=345 nm. FIG. 11B is a simplified chart showing the energy transfer processes (black curved lines). FIG. 11C is a PL spectra of $^1O_2$ registered upon excitation at 420 nm of SiNC($C_{11}$)Py upon addition of $C_{60}$ (1.5×10$^-$5M, solid line), compared to that of $C_{60}$ (1.5×10$^{-5}$M, dotted line) in toluene upon excitation at 330 nm for optically matched solutions at the excitation wavelength. For comparison purposes, the tail of the PL spectra of silicon nanocrystals has been subtracted.

FIG. 23A is the transient absorption spectra of SiNC(C$_{11}$)Py (diameter 3 nm) in degassed toluene in the absence (dark grey line) and in the presence of C$_{60}$ (1.5×10$^{-5}$M (black solid line) compared to a degassed toluene solution of C$_{60}$ (1.5×10$^{-5}$M, light grey line) upon excitation at 532 nm. FIG. 23B is the normalized transient absorption decays at 735 nm of SiNC(C$_{11}$)Py in the absence (grey line) and in the presence of C$_{60}$ (black line) compared to C$_{60}$ (light grey line). The emission intensity decay at 645 nm of SiNC(C$_{11}$)Py in the presence of C$_{60}$ (black dashed line) is displayed for comparison purposes.

FIG. 24A and FIG. 24B are SEM micrographs of the SiNCs deposited onto the graphene coated area of the Si/SiO$_2$ wafer (FIG. 24A), with a visible graphene wrinkle, and outside the graphene area, on the pristine SiO$_2$ layer (FIG. 24B). The nanocrystals are forming a continuous and equally distributed layer (darker areas). Scale bar equal to 50 nm.

DETAILED DESCRIPTION

Figures 1A, 1B, 1C:
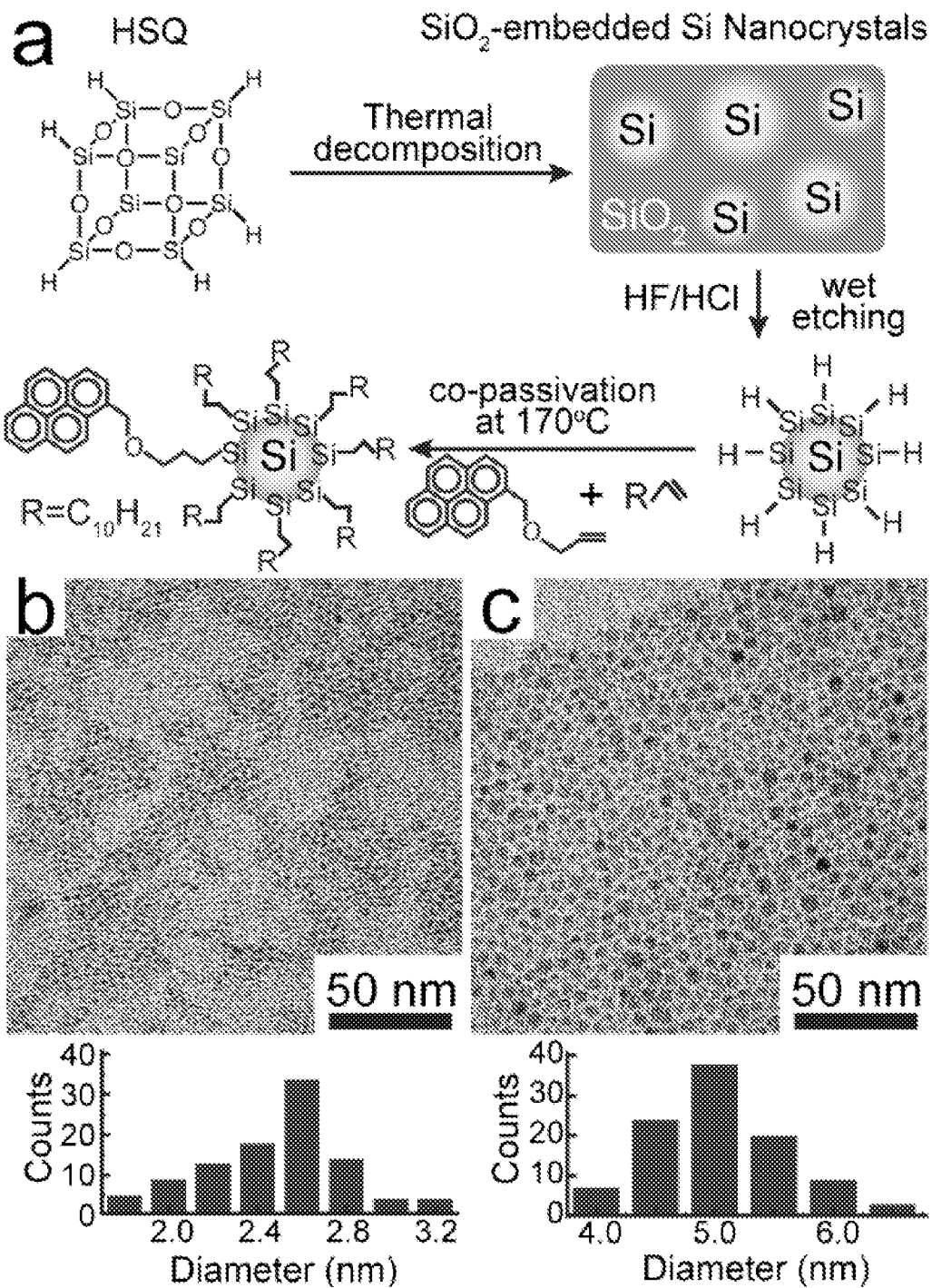
FIG. 1A shows a synthetic scheme for SiNC and SiNC-Py nanocrystals and the diameter of the SiNC-Py nanocrystals.
FIG. 1B and FIG. 1C are TEM images and bar graphs showing the average Si core diameter for 2.6 nm (FIG. 1B) and 5.0 nm (FIG. 1C) SiNC-Py nanocrystals.

The systems, compositions, and methods described herein may be understood more readily by reference to the following detailed description of specific aspects of the disclosed subject matter and the Examples and Figures included therein.

Before the present systems, compositions, and methods are disclosed and described, it is to be understood that this disclosure is not limited to specific synthetic methods or to particular reagents, as such may, of course, vary. It is also to be understood that the terminology used herein is for the purpose of describing particular embodiments only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the system" includes mixtures of two or more such systems, reference to "a luminescent chromophore" includes mixture of two or more such chromophores, and the like.

"Optional" or "optionally" means that the subsequently described event or circumstance can or cannot occur, and that the description includes instances where the event or circumstance occurs and instances where it does not.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

Terms used herein will have their customary meaning in the art unless specified otherwise. The organic moieties mentioned when defining variable positions within the general formulae described herein (e.g., the term "alkenyl") are collective terms for the individual substituents encompassed by the organic moiety.

The term "alkenyl," as used herein, refers to aliphatic carbon chains which have at least one carbon-carbon double bond. In some examples, alkenyl groups can include C$_2$-C$_{20}$ alkenyl groups. In other examples, alkenyl can include C$_2$-C$_{12}$, C$_2$-C$_{10}$, C$_2$-C$_8$, C$_2$-C$_6$, or C$_2$-C$_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "C$_2$-C$_{10}$-alkenyl" groups can include more than one double bond in the chain. The one or more unsaturations within the alkenyl group can be located at any position(s) within the carbon chain as valence permits. In some examples, when the alkenyl group is covalently bound to one or more additional moieties, the carbon atom(s) in the alkenyl group that are covalently bound to the one or more additional moieties are not part of a carbon-carbon double bond within the alkenyl group. Examples of alkenyl groups include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1- butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl groups.

"Aliphatic", as used herein, refers to unsaturated groups containing carbon and hydrogen, including straight-chain alkenyl, branched-chain alkenyl, cycloalkenyl, alkyl substituted cycloalkenyl, and cycloalkyl substituted alkenyl groups. Unless otherwise indicated, a straight chain or branched chain aliphatic group has 20 or fewer carbon atoms in its backbone (e.g., $C_2$-$C_{20}$ for straight chain, $C_4$-$C_{20}$ for branched chain). In some embodiments, the chain has 2-12 carbons. Likewise, cycloalkenyls can have from 3-10 carbon atoms in their ring structure, more preferably have 5, 6, or 7 carbons in the ring structure. The ranges provided above are inclusive of all values between the minimum value and the maximum value.

The alkenyl group can be substituted or unsubstituted. As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

Reference will now be made in detail to specific aspects of the disclosed materials, compounds, compositions, articles, and methods, examples of which are illustrated in the accompanying Examples and Figures.

Systems

Systems comprising a nanocrystal (also referred to herein as quantum dots, semiconductors, and/or NC) are disclosed herein. "Nanocrystal" refers to a semiconductor crystal with a nanoscale diameter, and because of its small size behaves like a potential well that confines electrons in three dimensions to a region on the order of the electrons' de Broglie wavelength in size, a few nanometers in a semiconductor. The nanocrystal can absorb energy of a first electromagnetic region and emit radiation in a second electromagnetic region; the particular absorbance or emission regions can depend upon the material and diameter of the nanocrystal.

The system can comprise a luminescent chromophore and a nanocrystal. The luminescent chromophore can emit energy having a first wavelength. Excitation of the luminescent chromophore by electromagnetic radiation having a second wavelength, such as by visible radiation, can result in emission of energy having a first wavelength. The luminescent chromophore is configured to transfer the emitted energy having a first wavelength to the nanocrystal. For example, the luminescent chromophore can be linked to the nanocrystal via a covalent bond. In other examples, the luminescent chromophore can be linked to the nanocrystal via a linker moiety of from 1 to 50 atoms. Absorption of the energy having first wavelength by the nanocrystal can activate the nanocrystal and result in an increase in quantum yield.

Nanocrystals

The nanocrystal that can be used in the system disclosed may be capable of absorbing energy of a first wavelength and emitting electromagnetic radiation (such as near infrared and visible light). In some embodiments, the nanocrystal can include a semiconductor that comprises a wide band gap. The band gap can be greater than 1 eV. In some embodiments, the band gap can be an indirect band gap. The nanocrystal can comprise a Group II to Group VI atom, or combinations thereof. In some embodiments, the nanocrystal can be a Group IV nanocrystal. Examples or suitable nanocrystal can include silicon, germanium, carbon, or combinations thereof.

In some examples, the nanocrystal can be biocompatible, such that the system is suitable for use in a variety of biological applications. "Biocompatible" or "biologically compatible", as used herein, generally refer to compounds or particles that are, along with any metabolites or degradation products thereof, generally non-toxic to cells and tissues, and which do not cause any significant adverse effects to cells and tissues when cells and tissues are incubated (e.g., cultured) in their presence. In some embodiments, the biocompatible nanocrystal can be degradable. In some embodiments, the biocompatible nanocrystal can be inert, that is, stable in biological environments. In some embodiments, the nanocrystal can be coated with a biocompatible material. The biocompatible material can be a lipid, a carbohydrate, a polysaccharide, a protein, a glycoprotein, a glycolipid, silica, alumina, titanium oxide or combinations thereof. Examples of suitable biocompatible nanocrystal include a silicon containing nanocrystal.

The system can exhibit unique optical properties that are a function of both the nanocrystal composition and physical size. Both the absorption and the photoluminescent wavelength are a function of the nanocrystal size and composition. The narrower the size distribution of the nanocrystals, the narrower the full-width half max (FWHM) of the resultant photoluminescent spectra. The average particle size of the nanocrystal can be from about 0.1 nm to about 100 nm, about 0.1 nm to about 50 nm, about 0.1 nm to about 25 nm, about 0.1 nm to about 20 nm, or about 1 nm to about 50 nm. For example, the average particle size of the nanocrystal can be about 10 nm or less, about 20 nm or less, about 30 nm or less, about 40 nm or less, about 50 nm or less, about 100 nm or less, about 200 nm or less, or about 250 nm or less. In some embodiments, the average particle size of the nanocrystal can be about 0.1 nm or greater, 0.5 nm or greater, 1 nm or greater, 1.5 nm or greater, 2 nm or greater, 2.5 nm or greater, 3 nm or greater, 3.5 nm or greater, 4 nm or greater, 4.5 nm or greater, 5 nm or greater, 6 nm or greater, or 10 nm or greater. The average particle size refers to the average particle size of the nanocrystal alone and/or in the systems provided herein. The nanocrystals can be spherical, approximately spherical, or nonspherical. In spherical cases, the diameter typically refers to the diameter of the nanocrystal. In nonspherical cases, the diameter typically refers to the diameter of a sphere having the same hydrodynamic volume of the nanocrystal.

Luminescent Chromophore

The systems can also contain a luminescent chromophore useful for transferring their emitted energy to the nanocrystal. In some examples, the emission spectrum of the luminescent chromophore can be matched to the absorption spectrum of the nanocrystal. In other examples, the emission spectrum of the luminescent chromophore can be partially overlapped with the absorption spectrum of the nanocrystal. In even other examples, the emission spectrum of the luminescent chromophore does not overlap with the absorption spectra of the nanocrystal.

The luminescent chromophore can emit energy in a first electromagnetic region when excited with electromagnetic radiation having a second wavelength. That is, the luminescent chromophore can emit energy having a first wavelength. In some embodiments, the luminescent chromophore can emit energy having a first wavelength in the visible or near infrared portions of the electromagnetic spectrum. In some embodiments, the luminescent chromophore can emit energy having a first wavelength of from about 250 nm to about 600 nm. For example, the first wavelength can be about 600 nm or less, about 550 nm or less, about 500 nm or less, about 450 nm or less, or about 400 nm or less. The first wavelength can be about 250 nm or greater, about 300 nm or greater, about 350 nm or greater, or about 400 nm or greater.

In some embodiments, the luminescent chromophore can be a biocompatible chromophore. Representative examples of the luminescent chromophore can be a cyclic organic complex such as organic dyes and pigments, oligomeric compounds, and conducting polymers. In some embodiments, the luminescent chromophore absorbs radiation of a second wavelength in the range of from about 300 nm to about 900 nm. Specific examples of suitable luminescent chromophore can include, but are not limited to, porphyrins; benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyoromethene, aza-boron dipyoromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, carbostyril; terbium complex; inorganic phosphor; ionophore such as crown ethers affiliated or derivatized dyes; or combinations thereof. Other examples of suitable luminescent chromophores can include, but are not limited to, Pd (II) octaethylporphyrin; Pt (II)-octaethylporphyrin; Pd (II) tetraphenylporphyrin; Pt (II) tetraphenylporphyrin; Pd (II) meso-tetraphenylporphyrin tetrabenzoporphine; Pt (II) meso-tetrapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra (pentafluorophenyl) porphyrin; Ru (II) tris (4,7-diphenyl-1,10-phenanthroline) (Ru (dpp)$_3$); Ru (II) tris (1,10-phenanthroline) (Ru(phen)$_3$), tris(2,2'-bipyridine)ruthenium (II) chloride hexahydrate (Ru(bpy)$_3$); erythrosine B; fluorescein; eosin; iridium (III) ((N-methyl-benzimidazol-2-yl)-7-(diethylamino)-coumarin)); indium (III) ((benzothiazol-2-yl)-7-(diethylamino)-coumarin))-2-(acetylacetonate); 3-coordination iridium complex having on a ligand 2,2'-bipyridine-4,4'-dicarboxylic acid, factris(2-phenylpyridine)iridium (Ir(Ppy)3), 8-hydroxyquinoline aluminum (Alq3), tris(4-methyl-8-quinolinolate)aluminum (III) (Almq3), 8-hydroxyquinoline zinc (Znq2), (1,10-phenanthroline)-tris-(4,4,4-trifluoro-1-(2-thienyl)-butane-1,3-dionate), europium (III) (Eu(TTA)3(phen)), 2,3,7,8,12,13,17,18-octaethyl-21H, and 23H-porphin platinum (II); Lumogen dyes; Macroflex fluorescent red; Macrolex fluorescent yellow; Texas Red; rhodamine B; rhodamine 6G; sulfur rhodamine; m-cresol; thymol blue; xylenol blue; cresol red; chlorophenol blue; bromocresol green; bromcresol red; bromothymol blue; Cy2; a Cy3; a Cy5; a Cy5.5; Cy7; 4-nitrophenol; alizarin; phenolphthalein; o-cresolphthalein; chlorophenol red; calmagite; bromo-xylenol; phenol red; neutral red; nitrazine; 3,4,5,6-tetrabromphenolphtalein; congo red; fluorescein; eosin; 2',7'-dichlorofluorescein; 5(6)-carboxyfluorecsein; carboxynaphtofluorescein; 8-hydroxypyrene-1, 3,6-trisulfonic acid; semi-naphthorhodafluor; semi-naphthofluorescein; tris (4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; and dioctadecylcycloxacarbocyanine; derivatives or combinations thereof.

In some embodiments, the luminescent chromophore can be pyrene or derivatives thereof, a fullerene or derivatives thereof, a naphthalimide or derivatives thereof, a perylene or derivatives thereof, a tetranitrogen macrocycle or derivatives thereof, a tetrapyrollic macrocycle or derivatives thereof, a phthalocyanine or derivatives thereof, a porphyrin or derivatives thereof, a metallated tetracyanoporphyrin or derivatives thereof, or combinations thereof. In some examples, the luminescent chromophore can be pyrene. The luminescent chromophore can be linked to the nanocrystal directly or indirectly.

The luminescent chromophore and the silicon containing nanocrystal can be in a ratio of about 1:1 to 100:1 in the nanocrystal system. For example, the luminescent chromophore and the silicon containing nanocrystal can be in a ratio of about 1:1 or greater, 5:1 or greater, 10:1 or greater, 15:1 or greater, 20:1 or greater, 25:1 or greater, 30:1 or greater, 35:1 or greater, 40:1 or greater, 50:1 or greater, 55:1 or greater, 60:1 or greater, 65:1 or greater, 70:1 or greater, 75:1 or greater, 80:1 or greater, 85:1 or greater, 90:1 or greater, or 100:1 or greater.

The systems described herein can exhibit a quantum yield. "Quantum yield" refers to the percent of absorbed photons that are reemitted as photons. In one aspect, the quantum yield of the system can be about 2% or greater, for example, about 3% or greater, about 4% or greater, about 5% or greater, about 6% or greater, about 7% or greater, about 8% or greater, about 9% or greater, about 10% or greater, about 12% or greater, about 15% or greater, about 20% or greater, about 25% or greater, about 30% or greater, about 35% or greater, about 40% or greater, about 45% or greater, about 50% or greater, about 55% or greater, about 60% or greater, about 65% or greater, about 70% or greater, about 75% or greater, about 80% or greater, about 85% or greater, about 90% or greater, or about 95% or greater. In some embodiments, the system can exhibit an increase in photoluminescence quantum yield of at least double that of the nanocrystal without the luminescent chromophore.

In some embodiments, a greater amount of energy having said second wavelength can be absorbed by the system than the silicon containing nanocrystal. In some embodiments, the amount of energy having said second wavelength absorbed by the system can be three times or greater, than energy absorbed upon direct excitation of the silicon containing nanocrystal.

The energy of said second wavelength can be transferred with at least 60% efficiency from the luminescent chromophore to the silicon containing nanocrystal. In one aspect, the energy of said second wavelength can be transferred with at least about 60% or greater, about 65% or greater, about 70% or greater, about 75% or greater, about 80% or greater, about 85% or greater, about 90% or greater, or about 95% or greater efficiency.

The radiation emitted from the system can be greater than the radiation emitted upon direct excitation of the silicon containing nanocrystal. In some embodiments, the system can exhibit a greater intensity of brightness than the silicon containing nanocrystal only. In some aspects, the system can exhibit a brightness intensity of greater than about 200% than the silicon containing nanocrystal. For example, the system can exhibit a brightness intensity of about 200% or greater, about C250% or greater, about 300% or greater, or about 350% or greater, than the silicon containing nanocrystal.

Linker

As noted, the luminescent chromophore can be linked to the nanocrystal indirectly; that is, through the use of a linker. The distance between the luminescent chromophore and the nanocrystal can have an effect on the energy transfer efficiency. In some examples, the linker can comprise a moiety reactive with the silicon containing nanocrystal. In some embodiments, the moiety reactive with the silicon containing nanocrystal can include an alkenyl group. The linker can be a C1 to C50 aliphatic chain. In some embodiments, the linker can be a straight chain alkyl, alkenyl, or alkynyl linker having from 1 to 50 atoms. In specific examples, the linker can be $C_1$-$C_{25}$, $C_6$-$C_{20}$, $C_{10}$-$C_{16}$ alkyl, alkenyl, or alkynyl. In a specific example, the linker can be at least $C_8$, $C_9$, $C_{10}$, $C_{11}$ or $C_{12}$ alkyl, alkenyl, or alkynyl. In a specific example, the linker can be a $C_{11}$ alkyl group. In other examples the linker can be a $C_2$, $C_3$, $C_4$, $C_5$, $C_6$, or $C_7$ alkyl, alkenyl, or alkynyl group. In a specific example, the linker can be a $C_3$ alkyl group.

Target Recognition Moiety

The specificity of the disclosed systems can be increased by conjugation of the system with a target recognition moiety, which specifically binds to a component on the surface of, for example, a target cell or tissue. Target recognition moiety includes cell recognition moieties which specifically bind to receptors on the surface of a target cell. A wide variety of natural and synthetic molecules recognized by target cells can be used as the target recognition moiety. Suitable target recognition moieties include, but are not limited to, a receptor, ligand, polynucleotide, peptide, polynucleotide binding agent, antigen, antibody, or combinations thereof. In one embodiment, the target recognition moiety is a peptide which has a length of from about 6 amino acids to about 25 amino acids. More specifically, the peptide amino acid sequence can be Cys-Asp-Cys-Arg-Gly-Asp-Cys-Phe-Cys (SEQ ID NO:1), which interacts with integrin $\alpha_v\beta_3$. Integrin $\alpha_v\beta_3$ is overexpressed on tumor vasculatures and tumor cells.

The target recognition moiety, for example the peptide amino acid sequence, can be similar, homologous, or a variant of target recognition moieties in the art. In general, variants of the target recognition moiety for example nucleic acids and peptides herein disclosed, can have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% similarity, or homology, to the stated sequence or the native sequence. Those of skill in the art readily understand how to determine the similarity of two polypeptides or nucleic acids. For example, the similarity can be calculated after aligning the two sequences so that the similarity is at its highest level. As an example, peptides can have one or more conservative amino acid substitutions. These conservative substitutions are such that a naturally occurring amino acid is replaced by one having similar properties. Such conservative substitutions do not alter the function of the peptide.

The following references discloses antibodies, receptors, or receptor ligands that can be used to target specific proteins to tumor tissue: (Senter, et al., *Bioconjugate Chem.*, 1991, 2:447-451; Bagshawe, K. D., *Br. J. Cancer*, 1989, 60:275-281; Bagshawe, et al., *Br. J. Cancer*, 1988, 58:700-703; Senter, et al., *Bioconjugate Chem.*, 1993, 4:3-9; Battelli, et al., *Cancer Immunol. Immunother.*, 1992, 35:421-425; Pietersz and McKenzie, *Immunolog. Reviews*, 1992, 129:57-80; and Roffler, et al., *Biochem. Pharmacol*, 1991, 42:2062-2065), disclosure of which are incorporated herein by reference. The following references discloses vehicles such as "stealth" and other antibody conjugated particles (including lipid mediated drug targeting to colonic carcinoma), receptor mediated targeting through cell specific ligands, lymphocyte directed tumor targeting, and highly specific therapeutic retroviral targeting of murine glioma cells in vivo: (Hughes et al., *Cancer Research*, 1989, 49:6214-6220; and Litzinger and Huang, *Biochimica* et *Biophysica Acta*, 1992, 1104:179-187), disclosure of which are incorporated herein by reference.

Compositions

The systems disclosed herein can be prepared as or formulated into a composition. In some examples, the systems can be formulated into a pharmaceutical composition. The pharmaceutical composition can contain a plurality of the systems describes and an acceptable excipient. The acceptable excipient can be administered with the nanocrystal system disclosed above.

In some embodiments, the compositions can be administered in vivo in a pharmaceutically acceptable carrier. By "pharmaceutically acceptable" is meant a material selected to minimize any degradation of the active ingredient and to minimize any adverse side effects in the subject, as would be well known to one of skill in the art. Suitable carriers and excipients are described in Remington: *The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semi permeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

The compositions can be administered orally, parenterally (e.g., via intravenous injection, intraperitoneal injection, by intramuscular injection, intratumoral injection, intraarterial injection, transdermally, extracorporeally, topically or the like, including topical intranasal administration or administration by inhalant, or a combination thereof. As used herein, "topical intranasal administration" means delivery of the compositions into the nose and nasal passages through one or both of the nostrils and can comprise delivery by a spraying mechanism or droplet mechanism, or through aerosolization of the compositions. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

It has also been found that the disclosed nanoparticle systems can interact with various carbon allotropes. Examples of such allotropes are carbon nanotubes (e.g., single and multiwalled nanotubes), graphene, and fullerenes. Additional energy transfer processes have been found to occur from the nanocrystals to these carbon materials, showing that the energy harvested by the hybrid antenna can promote successive photoinduced processes. Thus, systems comprising the disclosed nanocrystals with linked chromophores and a carbon allotrope are disclosed herein.

Methods of Making

Methods of synthesizing the systems described herein are provided. For example, for the synthesis of a silicon containing nanocrystal covalently bound to pyrene, the method can include providing the silicon containing nanocrystal. Providing the silicon containing nanocrystal can include synthesizing the nanocrystal by drying an organosilicone compound, such as silsesquioxane followed by heating the compound in a furnace. The silicon containing compound can be heated up to 1200° C. at a heating rate of 18° C./min. The temperature is held for about an hour. The reaction product can be etched with concentrated acid, such as hydrofluoric and hydrochloric acid, in the dark for about 4 to 6 hours. The mixture is then purified by centrifugation for example at about 8000 rpm for 5 min then rinsed to yield the silicon containing nanocrystals.

The silicon containing nanocrystals can then be dispersed in a solution of the luminescent chromophore followed by heating. In some embodiments, the dispersion can be put through one or more freeze-pump-thaw cycles before heating. The dispersion can then be heated from about 150° C. to about 200° C. for from about 10 hours to about 15 hours. For example, the dispersion can be heated at 170° C. for about 12 hours to give the silicon containing nanocrystal system.

In some examples, a linker can also be conjugated to the nanocrystal. The linker can comprise a moiety reactive with the silicon containing nanocrystal and the luminescent chromophore. In some embodiments, the moiety reactive with the silicon containing nanocrystal can include an alkenyl group or a halide. The linking agent can be a C1 to C50 aliphatic chain. In some embodiments, the linking agent can be a straight chain aliphatic group (alkyl, alkenyl, or alkynyl). The linking agent can be combined with the luminescent chromophore to form a mixture. The silicon containing nanocrystals can then be dispersed in the mixture of the luminescent chromophore and the linker. The luminescent chromophore and the linking agent can be in a ratio of from 1:1 to 1:50. For example, luminescent chromophore and the linking agent can be in a ratio of 1:1 or less, 1:10 or less, 1:15 or less, 1:20 or less, 1:25 or less, 1:30 or less, 1:40 or less, or 1:50 or less. The nanocrystal system can be purified by centrifugation followed by rinsing to yield the silicon containing nanocrystal system.

Methods of Use

The nanocrystals disclosed herein have potential applications in a number of fields such as solar cells, optoelectronic devices and fluorescent bio-labelling agents. In some embodiments, the nanocrystals can be used in bioanalytical devices such as DNA chips, miniaturized biosensors and microfluidic devices. Further, the nanocrystals can be used in applications benefiting from fluorescent labeling including medical and non-medical fluorescence microscopy, histology, flow cytometry, fundamental cellular and molecular biology protocols, fluorescence in situ hybridization, DNA sequencing, immuno assays, binding assays and separation. In particular, the nanocrystals can be used in gene expression profiling, drug discovery, and clinical diagnostics. For example, a conjugate, in which a nanocrystal is linked to a target moiety that has an affinity for a biological target, can be used as sensors to detect the presence or amounts of a biological moiety; the structure, composition, and conformation of a biological moiety; the localization of a biological moiety in an environment; interactions of biological moieties; alterations in structures of biological compounds; and alterations in biological processes. In some embodiments, the nanocrystal systems can be used for tumor imaging.

The systems can also be used as a frequency converter. The systems can also be used in a light emitting diode device, for example a light emitting diode, capable of providing energy above the band gap energy of the nanocrystal system. The systems can also be used in a modified fluorescent light source as well as in electroluminescent devices based on emission nanocrystals.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

$^1$H-NMR and $^{13}$C-NMR spectra were recorded on Varian NOVA 400 (400 MHz) spectrometers. Chemical shifts are reported in ppm using tetramethylsilane as the internal reference standard. Data are reported as follows: chemical shift, multiplicity (s=singlet, d=doublet, t=triplet, q=quartet, br=broad, m=multiplet), coupling constants (Hz). LC-electrospray ionization mass spectra were obtained with an Agilent Technologies MSD1100 single-quadrupole mass spectrometer. Chromatographic purification was performed on 240-400 mesh silica gel. All reactions were carried out under a nitrogen atmosphere in flame-dried glassware using standard inert techniques for introducing reagents and solvents. Melting points are uncorrected.

Hydrogen silsesquioxane (flowable oxide, solution in methyl isobutyl ketone and toluene) was purchased from Dow Corning, hydrofluoric acid (48% in $H_2O$), 1-dodecene, 1-pyrenemethanol, sodium hydride, 11-bromide-1-undecene were purchased from Sigma Aldrich. $C_{60}$ was a commercial high-purity product from Sigma-Aldrich. SWCNTs were Unidym Superpurified #SP2167 sample provided by Prof Davide Bonifazi.

Transmission Electron Microscopy (TEM) characterization was carried out with a FEI Tecnai F20 instrument, equipped with a Schottky emitter and operated at 200 keV. High Resolution (HRTEM) and Scanning Transmission (STEM) High Angle Annular Dark Field (HAADF) imaging were extensively employed. TEM samples were made by drop casting toluene dispersions onto carbon coated 200 mesh copper TEM grids (Electron Microscopy Science). The nanocrystal size was determined manually, on the basis of the acquired HRTEM and STEM images.

Photophysical measurements were carried out in air-equilibrated or deaerated toluene solution at 298 K. Solutions were deaerated by freeze-pump-thaw cycles. UV-visible absorbance spectra were recorded with a Perkin Elmer λ650 spectrophotometer, using quartz cells with 1.0 cm path length. Emission spectra were obtained with a Perkin Elmer LS-50 spectrofluorometer, equipped with a Hamamatsu R928 phototube, or an Edinburgh FLS920 spectrofluorometer equipped with a Ge-detector for emission in the NIR spectral region. Correction of the emission spectra for detector sensitivity in the 700-1200 nm spectral region was performed. Emission quantum yields were measured following the method of Demas and Crosby (*J. Phys. Chem.* 1971, 75:991-1024) (standard used: [Ru(bpy)$_3$]Cl$_2$ in air-equilibrated water $\Phi_{PL}$=0.040 (Suzuki, et al. *Phys. Chem. Chem. Phys.* 2009, 11:9850-9860), 1,1',3,3,3',3'-hexamethylindotricarbocyanine iodide (HITCI) in air-equilibrated ethanol $\Phi_{PL}$=0.30) (Würth, et al. *Nat. Protoc.* 2013, 8:1535-1550). Luminescent excited state lifetimes in the range 0.5 ns to 1 μs were measured by an Edinburgh FLS920 spectrofluorometer equipped with a TCC900 card for data acquisition in time-correlated single-photon counting experiments (0.2 ns time resolution) with a 340 nm pulsed diode and a LDH-P-C-405 pulsed diode laser. Emission intensity decay measurements in the range 10 μs to 1 s were performed on a Perkin Elmer LS-50 spectrofluorometer equipped with a pulsed Xe lamp.

The experiments of ns-transient absorption spectroscopy on silicon nanocrystals were performed by an Ultrafast Systems apparatus equipped with a Hamamatsu R928 phototube connected to a Tektronix TDS380 (400 MHz) oscilloscope and a Continuum Surelite I-10 Nd:YAG laser source ($\lambda_{ex}$=532 nm).

Wide-field luminescence microscopy was carried out by an Olympus IX 71 inverted microscope equipped with a Xenon lamp (450 W) for fluorescence excitation and a Basler Scout scA640-70 gc CCD camera for image acquisition. The lamp was attenuated with an absorptive filter Thorlabs NE30B and coupled to a fluorescence cube mounting the filters set Chroma 11001v2 blue. Images with 40× magnification were taken using the objective Olympus UPL-FLN 40×.

The estimated experimental errors are: 2 nm on the absorption and PL band maximum, 5% on the molar absorption coefficient and luminescence lifetime, and 10% on the luminescence quantum yield.

Example 1: Silicon Nanocrystals Functionalized with Pyrene Units 1-(Allyloxymethyl)Pyrene Synthesis.

Sodium hydride (0.124 g, 5.16 mmol, 1.2 eq) was added to a mixture of 1-pyrenemethanol (1.00 g, 4.30 mmol, 1 eq), propargyl bromide (0.645 g, 5.33 mmol, 1.24 eq) in $CH_3CN$ (25 mL) at 70° C. The reaction mixture was stirred vigorously for 24 h at 70° C. After completion of the reaction, three drops of $H_2O$ were added to the reaction mixture to quench the reaction. The mixture was extracted into chloroform (3×5 mL). The chloroform layer was dried over $MgSO_4$ and the solvent was removed under reduced pressure to give the crude product. The resulting residue was purified by silica column chromatography (Hexane/EtOAc 8:2), to give the product as a yellow solid (750 mg, yield=66%).

$^1$H-NMR (400 MHz, CDCl$_3$) δ: 8.38 (d, J=9.2 Hz, 1H); 8.23-8.20 (m, 2H); 8.17-8.13 (m, 2H); 8.08-8.03 (m, 4H); 6.21-6.14 (m, 1H); 5.51 (dd, J$_1$=1.6 Hz, J$_2$=1.6 Hz, 1H); 5.39 (dd, J$_1$=1.6 Hz, J$_2$=1.6 Hz, 1H); 5.24 (s, 2H); 4.25-4.23 (m, 2H).

$^{13}$C-NMR (100 MHz, CDCl$_3$) δ: 134.9, 131.4; 131.3; 131.2; 130.8; 129.2; 127.6; 127.4; 127.3; 126.8; 125.8; 125.2; 125.1; 124.9; 124.7; 124.5; 123.3; 117.3; 71.2, 70.6.

ESI-MS: 232 [M-C$_3$H$_5$]$^+$.

SiNC and SiNC-Py Synthesis:

Various synthetic methodologies have been reported for colloidal SiNCs (Kelly, Id.; Mangolini, et al. *Nano Lett.* 2005, 5:655-659; Li, et al. *Langmuir* 2003, 19, 8490-8496; Kang, et al. *J. Am. Chem. Soc.* 2007, 129:5326-5327; He, et al. *J. Am. Chem. Soc.* 2011, 133:14192-14195; Rosso-Vasic, et al. *Small* 2008, 4:1835-1841; Warner, et al. *Angew. Chem. Int. Ed.* 2005, 44:4550-4554). One route to SiNCs that provides systematic and widely tunable size and emission color utilizes hydrogen silsesquioxane (HSQ) as a starting material to produce oxide-embedded SiNCs that can be liberated by etching and passivated with an alkyl ligand monolayer by thermal hydrosilylation in the presence of alkene capping ligands (Hessel, et al. *Chem. Mater* 2006, 18:6139-6146; Hessel, et al. *Small* 2010, 6:2026-2034). These SiNCs can be produced with a reliable size, surface passivation, solvent dispersibility, stability and luminescence color. The photoluminescence (PL) quantum yield can reach values as high as 45% with lifetimes in the range of hundreds of μs (Locritani, et al. *J. Phys. Chem. Lett.* 2014, 5:3325-3329).

Here, hydride-terminated SiNCs were produced by a hydrogen silsequioxane (HSQ) decomposition route followed by thermal hydrosilylation with alkenes (see Hessel, et al. Small 2010, 6:2026-2034). The synthetic approach yielded clean, well-characterized nanocrystals with reliable control over size, surface passivation, emission color, dispersibility and photostability. Specifically, Si nanocrystals were synthesized as follows. 30 mL of flowable oxide (Dow Corning; 16 wt % hydrogen silsesquioxane (HSQ) in isobutyl methyl ketone) was dried under vacuum on a schlenk line for 6 hours to form a white residue of HSQ, which is then transferred to a tube furnace. After purging with forming gas (93% N$_2$, 7% H$_2$), the tube furnace is heated to 1 100° C. (2.6 nm diameter) or 1200° C. (5.0 nm diameter) at a heating rate of 18° C./min and then held at that temperature for an hour. The reaction product was etched with 48% HF and 37.5% HCl (10:1 v/v) in the dark for 4-6 hours and then centrifuged at 8000 rpm for 5 min. The nanocrystals were then rinsed once with deionized (DI) water, twice with ethanol, and once with chloroform. The nanocrystals were dispersed in either 5 mL of 1-dodecene, or 5 mL of 1-dodecene with 0.1 mL of 1-(allyloxymethyl)pyrene (1:36 pyrene:dodecene molar ratio) or 0.3 mL of 1-(allyloxymethyl)pyrene (1:12 pyrene:dodecene molar ratio). The initially turbid dispersions were put through three freeze-pump-thaw cycles, and then heated to 170° C. under $N_2$ flow for 12 hours. Over time, the dispersions became optically clear, indicating that passivation of Si nanocrystals had occurred. The nanocrystals were then purified by transfer to a glass centrifuge tube and centrifugation at 8000 rpm for 5 min. Poorly capped nanocrystals precipitated from the mixture were discarded. The supernatant was transferred to another glass centrifuge tube and washed with four consecutive centrifugation/precipitation cycles using toluene/ethanol solvent/antisolvent pair. The final SiNC and SiNC-Py samples were dispersed in toluene at a concentration of 5 mg/mL until further characterization.

$^1$H NMR spectra of SiNC and SiNC-Py with an average diameter of 2.6 nm (Py:dodecene ratio of 1:36 used in the passivation) dispersed in $CDCl_3$ at room temperature provided evidence of a covalently linked surface layer. The $^1$H NMR spectra of SiNC showed a uniform chemical environment for the alkyl chains with a single methyl resonance and several distinct methylene resonances. The $^1$H NMR spectrum of SiNC-Py showed additional signals compared to SiNC attributable to pyrene moieties. The molar ratio of pyrene appended groups and dodecene alkyl chains on the Si nanocrystals determined by integration of the relevant resonances in the $^1$H NMR spectra was 1:20, which is close to the Py:dodecene molar ratio (1:36) used in the passivation step.

FIGS. 2A-2D show TEM images of the 2.6 nm and 5.0 nm diameter SiNC and SiNC-Py samples used in this example. Py functionalization does not affect the size of the Si nanocrystals.

Figure 4A:
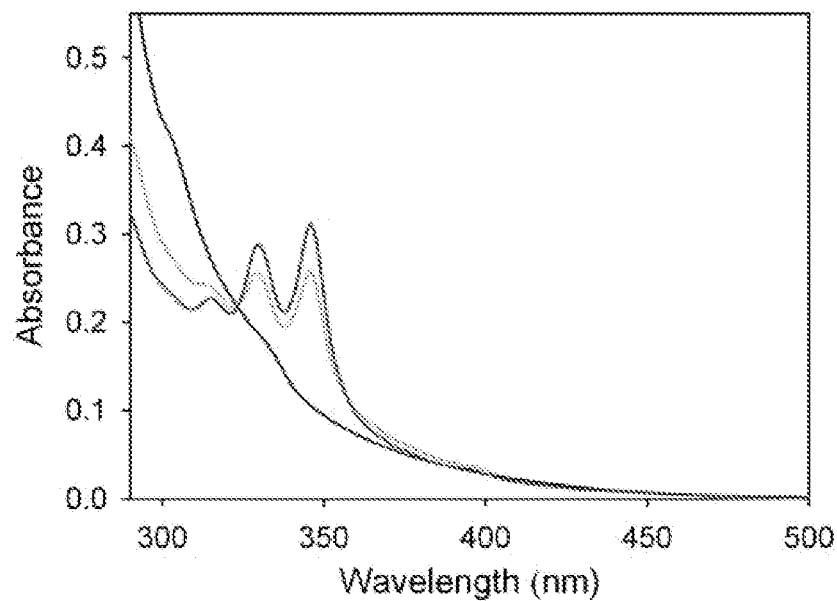
FIG. 4A and FIG. 4B show absorbance and photoluminescence spectra. The absorbance (FIG. 4A) and photoluminescence (FIG. 4B) spectra (b, $\lambda_{ex}$=378 nm) of 2.6 nm diameter SiNC (black) and SiNC-Py made with pyrene:dodecene molar ratios of 1:12 (dark grey line) and 1:36 (light grey line) dispersed in air-equilibrated toluene are shown. The solutions were optically matched at the excitation wavelength.
Figure 4B:
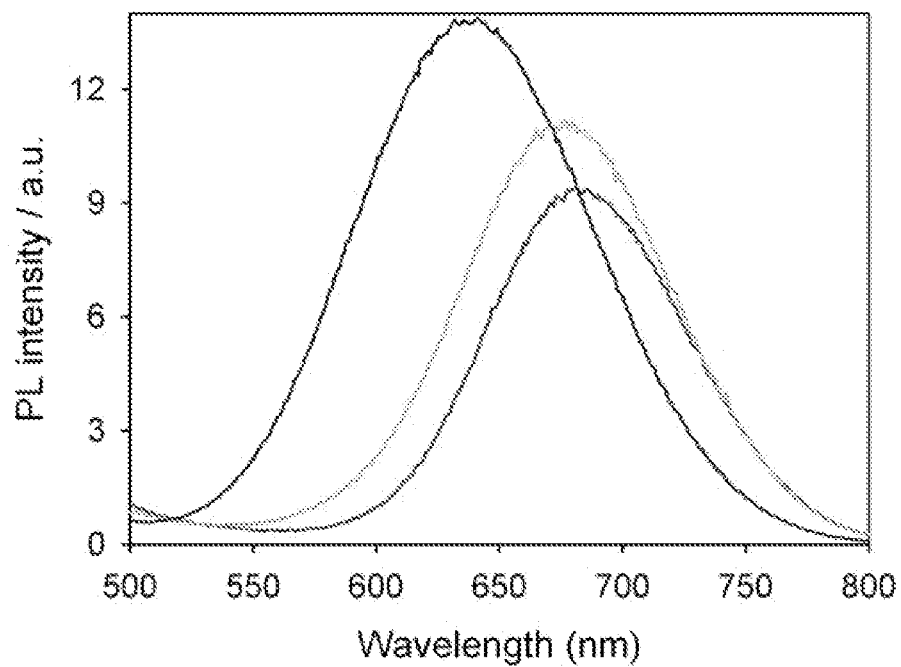
Figure 5:
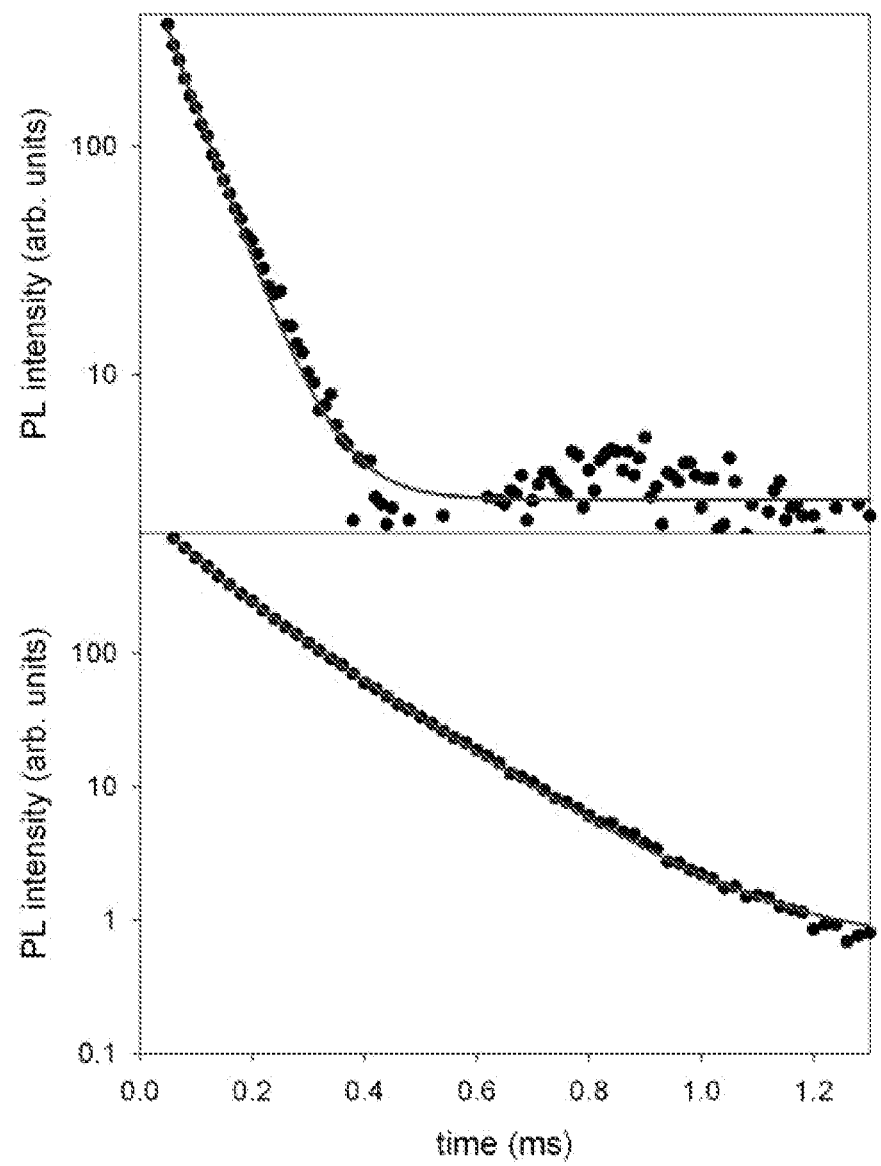
FIG. 5 shows a plot of the photoluminescence intensity decay at 635 nm (top) and 970 nm (bottom) for SiNC with diameters of 2.6 and 5.0 nm, respectively, dispersed in air-equilibrated toluene. ($\lambda_{ex}$=400 nm).
Figure 6:
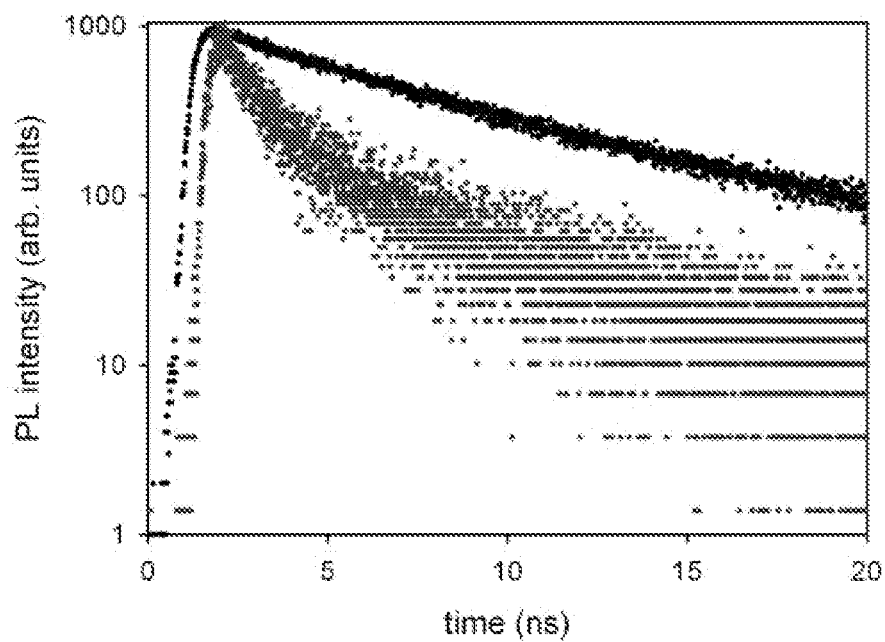
FIG. 6 shows a plot of the photoluminescence intensity decay at 400 nm ($\lambda_{ex}$=345 nm) of 2.6 nm diameter SiNC-Py made with pyrene:dodecene molar ratios of 1:12 (grey trace) and Py (black trace) in air equilibrated toluene.
Figure 7A:
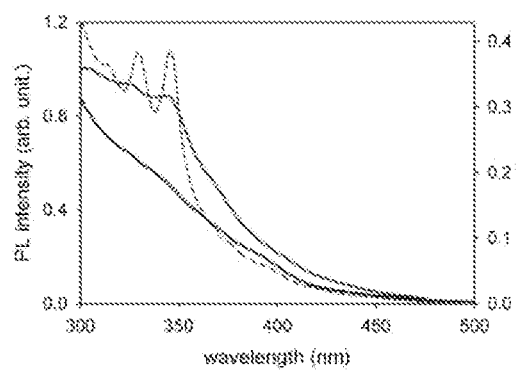
FIG. 7A and FIG. 7B are plots showing the photoluminescence excitation (PLE) spectra of 2.6 nm and 5.0 nm diameter SiNC-Py (dark grey solid line) and SiNC (black solid line) recorded with $\lambda_{em}$=660 and 780 nm. The absorption spectra of SiNC-Py are reported (dashed line).
Figure 7B:
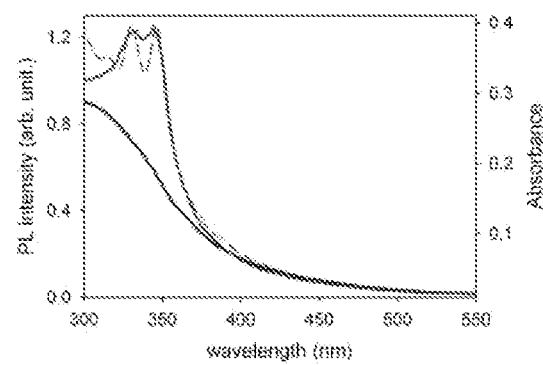

FIG. 4A shows absorbance spectra and FIG. 4B shows PL emission spectra (b, λex=378 nm) for 2.6 nm diameter SiNC and SiNC-Py made with pyrene:dodecene molar ratios of 1:12 (dark grey line) and 1:36 (light grey line) dispersed in air-equilibrated toluene. The solutions are optically matched at the excitation wavelength. For most SiNC samples, the peak emission wavelength shifted to slightly longer wavelength after derivatization with pyrene. For example, FIG. 4B shows the Si nanocrystal emission band shifted from 635 to 680 nm upon pyrene functionalization with a decrease of the emission quantum yield by about 30% (τ=95 µs). The red-shift and decrease in the emission quantum yield is slightly higher with increasing Py:dodecene ratio. FIG. 5 shows the photoluminescence intensity decay for PL emission at 635 nm and 970 nm for SiNC with diameters of 2.6 and 5.0 nm, respectively, dispersed in air-equilibrated toluene. (λex=400 nm). FIG. 6 shows the photoluminescence intensity decay at 400 nm (λex=345 nm) of 2.6 nm diameter SiNC-Py made with pyrene:dodecene molar ratios of 1:12 (grey trace) and Py (black trace) in air-equilibrated toluene. FIG. 7A and FIG. 7B show photoluminescence excitation (PLE) spectra of the 2.6 nm and 5.0 nm diameter SiNC-Py measured by monitoring the Si nanocrystal-related emission. The appearance of the pyrene-related absorption peaks confirms that pyrene-absorption followed by energy transfer to the nanocrystals is occurring.

Evaluation of the Efficiency of Energy Transfer.

Figure 3A:
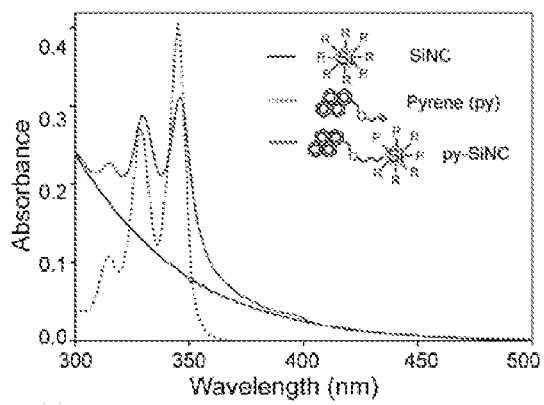
FIGS. 3A-3D show absorbance and photoluminescence spectra. The absorbance spectra of 2.6 nm (FIG. 3A) and 5.0 nm (FIG. 3C) diameter SiNC (black), SiNC-Py (grey line) and Py (black dotted line) in air-equilibrated toluene are shown. The photoluminescence (PL) spectra of 2.6 nm (FIG. 3B) and 5.0 nm (FIG. 3D) diameter SiNC-Py (solid black line, λex=345 nm; dashed black line, λex=378 nm) and optically matched solutions of free Py mixed with SiNCs in the appropriate ratio (light grey lines, λex=345 nm) in air-equilibrated toluene are shown. To obtain the PL spectra in FIG. 3B and FIG. 3D, the two samples of SiNC-Py photoexcited at 345 nm and 378 nm were optically matched at the excitation wavelength to enable direct comparison of the emission intensity of the Si nanocrystals when light absorption is dominated by the pyrene moieties or the nanocrystals.
Figure 3B:
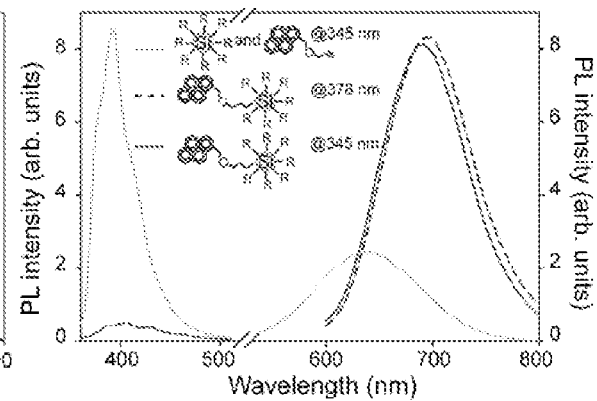
Figure 3C:
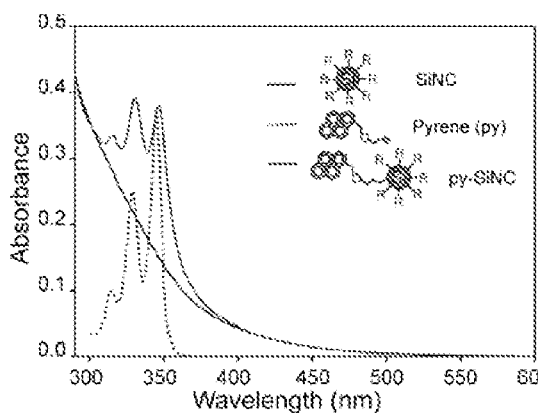
Figure 3D:
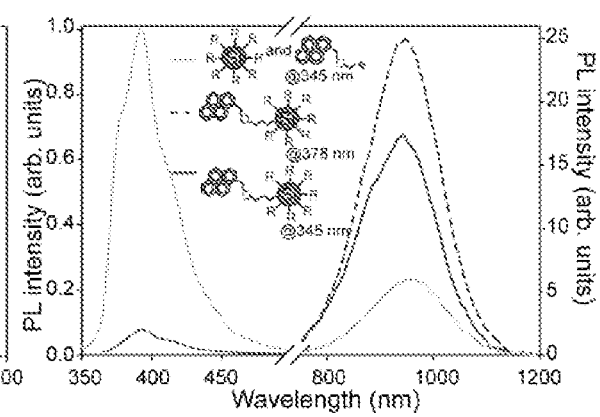

The efficiency of energy transfer can be estimated from the spectra shown in FIG. 3B and FIG. 3D as detailed in the following:

$$\eta_{en.tr.}=(I_{obs}-I_0)/(I_{100}-I_0)$$

where $I_{obs}$ is the area of the emission spectra observed for the SiNC-Py excited at 345 nm (dashed black line in FIG. 3B and FIG. 3D), in which both pyrene and the Si core absorb light; $I_0$ is the area of the emission spectrum observed for the mixture of SiNC and Py in a proper ratio to match the absorbance spectrum of the previous solution in the entire range (light grey line in FIG. 3B and FIG. 3D); $I_{100}$ is the area of the emission spectra observed for SiNC-Py excited at 378 nm (solid black line in FIG. 3B and FIG. 3D), in which only the Si core is absorbing light, for a solution having the same absorbance at the excitation wavelength of the first case.

$I_0$ represents the emission intensity expected when energy transfer does not take place and the Si core emission is obtained only by the light at 345 nm directly absorbed by the Si core. $I_0$ has been corrected to take into account the different emission quantum yield of the Si core upon direct excitation of the silicon core for SiNC and SiNC-Py, i.e. 0.45 vs 0.40 for 5.0 nm diameter nanoparticles, respectively (Table 1).

$I_{100}$ represents the emission intensity expected when energy transfer takes place with 100% efficiency and all the absorbed light results in the Si core emission.

Figure 8A:
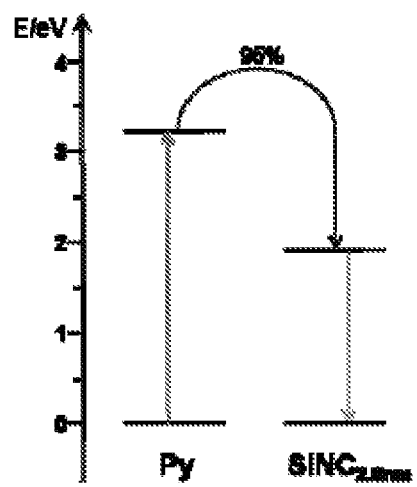
FIG. 8A and FIG. 8B are an energy level diagrams showing the energy transfer processes and the corresponding efficiency occurring in SiNC-Py of diameter 2.6 (FIG. 8A) and 5.0 nm (FIG. 8B) upon photoexcitation of the pyrene units.
Figure 8B:
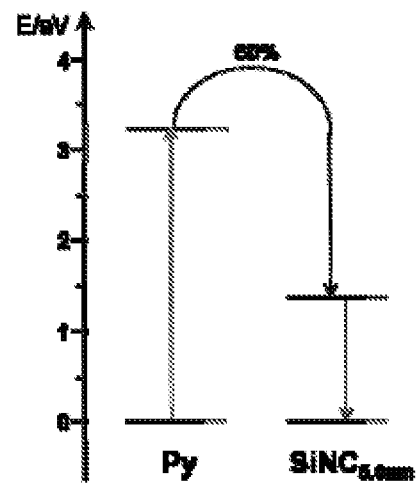

FIG. 8A and FIG. 8B show a schematic representation of the energy transfer process occurring in the 2.6 nm and 5.0 nm diameter SiNC-Py.

Results.

Nanocrystals were passivated with a mixed ligand layer of 1-dodecene and 1-(allyloxymethyl)pyrene (Py) using Py:dodecene molar ratios ranging between 0.025 and 0.08 (SiNC-Py), as described above and illustrated in FIG. 1A. For comparison, SiNCs were also passivated only with 1-dodecene (SiNC). FIG. 1B and FIG. 1C show TEM images and size histograms of the SiNC-Py materials studied. Two SiNC-Py samples were examined and used in this example for photophysical characterization with average Si core diameters of 2.6 nm and 5.0 nm. $^1$H and $^{13}$C NMR confirmed covalent pyrene functionalization on the SiNC-Py.

UV-vis-NIR absorbance and photoluminescence (PL) spectra of toluene dispersions of the 2.6 nm and 5.0 nm diameter SiNC and SiNC-Py are shown in FIGS. 3A-3D. SiNCs (without pyrene derivatization) exhibit an unstructured absorption profile that tails past 500 nm that is characteristic of Si nanocrystals (black curves in FIG. 3A and FIG. 3C). Free Py (FIG. 3A and FIG. 3C, black dotted lines) has a structured absorption band with three distinctive peaks appearing in the 300-350 nm region. The pyrene absorption peaks are clearly visible in the SiNC-Py absorbance spectra (grey curves in FIG. 3A and FIG. 3C). The number of pyrene units attached to each Si nanocrystal can be estimated from the relative absorbance of the structureless sloping background associated with the Si nanocrystals and the peaked absorption from the pyrene. On the basis of the molar absorption coefficients for Py, 2.6 nm diameter SiNCs and 5.0 nm diameter SiNCs of $\varepsilon_{346\ nm}$ (Py)=4.4×10$^4$ M$^{-1}$cm$^{-1}$, $\varepsilon_{400\ nm}$ (SiNC$_{2.6\ nm}$)=5×10$^4$ M$^{-1}$cm$^{-1}$ and $\varepsilon_{400\ nm}$ (SiNC$_{5.0\ nm}$)=5.3×10$^5$ M$^{-1}$cm$^{-1}$, there are approximately 8 and 6 pyrene units per nanocrystal for 2.6 nm diameter SiNC-Py made with Py:dodecene ratios of 1:12 (grey curve in FIG. 3A) and 1:36 (light grey curve in FIG. 4A) and ca. 60 Py units per nanocrystal on the 5.0 nm diameter SiNC-Py.

PL spectroscopy was performed to determine the extent of photogenerated energy transfer between pyrene groups attached to Si nanocrystals in the SiNC-Py samples. The PL spectra in FIG. 3B and FIG. 3D show that free Py and Py attached to SiNCs both luminesce with peak emission at ca. 400 nm. There is no evidence of Py excimer emission, which would occur at longer wavelength close to 500 nm. FIG. 3B and FIG. 3D also show PL spectra of SiNCs with 2.6 nm and 5.0 nm diameter, which exhibit PL emission peaks at 635 nm and 970 nm, respectively. Pyrene functionalization did not significantly affect the PL peak maxima of the 5.0 nm nanocrystals, but resulted in a slight red shift of the PL for the 2.6 nm nanocrystals to 680 nm (FIG. 4A and FIG. 4B). The PL spectra of 2.6 nm diameter and 5.0 nm diameter SiNC-Py are also shown in FIG. 3B and FIG. 3D, respectively. Excitation wavelengths of $\lambda_{ex}$=378 nm or $\lambda_{ex}$=345 nm were used to photoexcite either the Si nanocrystal core without significant pyrene photoexcitation or to predominantly photoexcite the pyrene units. Py does not absorb 378 nm light (see absorbance spectra in FIG. 3A and FIG. 3C), while the majority of the 345 nm light is absorbed by pyrene (for the 2.6 nm diameter SiNC-Py, pyrene absorbs 67% of the light). The PL emission spectra of the SiNC-Py in FIG. 3B and FIG. 3D were obtained by optically matching the SiNC-Py dispersions (by dilution) at the excitation wavelength to ensure that the PL spectra were measured with matching photon absorption at 378 and 345 nm. PL spectra of SiNCs and free Py mixed with the appropriate ratios to match the SiNC-Py absorbance profiles were also measured for comparison (the light grey curves in FIG. 3B and FIG. 3D).

Energy transfer from pyrene units bound to Si nanocrystals is shown by comparing the PL spectra of the SiNC-Py dispersions and the simple mixtures of SiNCs and free Py observed upon excitation with 345 nm light. When Py is not attached to the nanocrystals, photoexcitation at 345 nm leads to emission spectra dominated by the 400 nm emission of pyrene, with a lesser contribution of SiNC emission at longer wavelength (light grey curves in FIG. 3B and FIG. 3D). In contrast, the emission spectra of the SiNC-Py dispersions are dominated by emission from the nanocrystals when photoexcited by 345 nm light, with very little pyrene emission. The Py-related emission band is highly quenched in both the 2.6 nm and 5.0 nm diameter SiNC-Py samples, indicating that significant energy transfer occurs in the SiNC-Py samples of both sizes (see FIG. 5). Photoluminescence excitation (PLE) spectra also confirmed that energy transfer occurred in the SiNC-Py (See FIG. 6).

Energy transfer from pyrene to Si nanocrystals in the SiNC-Py sample is also shown in the measurement of the 400 nm fluorescence lifetime. The characteristic lifetime of free pyrene chromophore of 18 ns is not observed and the emission intensity decay of SiNC-Py at 400 nm cannot be fitted to a monoexponential function: one component is below the instrumental resolution (<0.2 ns) and the second one is ca. 5 ns (FIG. 6). These data confirm that the observed PL at 400 nm from the SiNC-Py sample excited at 345 nm is not due to free pyrene in solution.

The energy transfer efficiency from bound Py to the SiNCs in the SiNC-Py was determined by comparing the SiNC-related PL quantum yields obtained with 345 nm and 378 nm photoexcitation. The PL emission quantum yield of the 2.6 nm diameter SiNCs is 11% (both in aerated and de-aerated solution) with a lifetime of 70 μs (FIG. 5). For the 2.6 nm diameter SiNC-Py, the SiNC-related PL quantum yields (680 nm emission) were nearly independent of the the photoexcitation wavelength: 345 nm (solid black line in FIG. 3B, predominantly Py photoexcitation) or 378 nm (dashed black line in FIG. 3B, light is absorbed only by the Si nanocrystal core). Energy transfer from the pyrene chromophores to the 2.6 nm diameter Si core in the SiNC-Py sample takes place with >95% efficiency. (A schematic representation of the energy transfer process is shown in FIG. 8A and FIG. 8B.) It is worth noting that pyrene functionalization enhances the brightness of the Si nanocrystal PL by 300%, as the absorbance of SiNC-Py at the excitation wavelength of 345 nm is three times higher than that of the SiNCs.

The pyrene emission is also strongly quenched (>90%) in the 5.0 nm diameter SiNC-Py sample (black curves, FIG. 3D) due to energy transfer. The 970 nm PL emission quantum yields of SiNC and SiNC-Py were very high. With 380 nm photoexcitation, the SiNC and SiNC-Py species exhibited PL quantum yields (970 nm) of 45% and 40%, respectively. The 970 nm PL emission was also insensitive to dioxygen and the luminescence decay of the SiNC and SiNC-Py fit to a monoexponential decay with lifetimes of 150 and 190 μs, respectively. The emission quantum yield is remarkably high compared to dye molecules emitting in the same spectral region, for which emission quantum yields higher than 30%, and it is comparable to the value recently reported for PbS and PbSe quantum dots. Based on the relative PL emission spectra for 5.0 nm diameter SiNC-Py photoexcited with 345 nm (dashed black curve in FIG. 3D) and 378 nm light (solid black curve in FIG. 3D), energy transfer from adsorbed pyrene to the Si nanocrystals occurred with 65% efficiency. With the three-fold enhancement in light absorption due to the adsorbed pyrene, a 40% PL quantum yield and 65% energy transfer efficiency from the pyrene to the Si nanocrystals, there is an effective enhancement in NIR PL brightness of 78%. The 5.0 nm diameter SiNC-Py species are rather remarkable NIR emitters.

Table 1 summarizes the photophysical properties of the SiNC-Py species. Energy transfer between adsorbed pyrene units and SiNCs occurs with relatively high efficiency and pyrene functionalization does not deteriorate the SiNC PL properties. This is an interesting family of nanocrystals resulting from a light-harvesting antenna that enhances the brightness by up to 300%. The 5.0 nm diameter SiNC-Py exhibit UV-sensitized NIR luminescence with remarkably high emission quantum yield and long lifetime (Table 1), even in the presence of dioxygen.

TABLE 1

Photophysical properties of SiNC and SiNC-Py dispersed in air-equilibrated toluene at 298K. For comparison, the model compound Py is also reported.

|  | d/nm | $\lambda_{ex}$/nm | $\lambda_{em}$/nm | $\Phi_{em}{}^a$ | $\tau$/ns$^b$ |
| --- | --- | --- | --- | --- | --- |
| SiNC | 2.6 | 378 | 635 | 0.11 | 70 × 10$^3$ |
| SiNC-Py | 2.6 | 345 | 400 | 0.005 | <0.2, 5 |
|  |  | 378 | 680 | 0.08 | 95 × 10$^3$ |
| Py | — | 345 | 400 | 0.06 | 18 |
| SiNC | 5.0 | 378 | 970 | 0.45 | 150 × 10$^3$ |
| SiNC-Py | 5.0 | 345 | 400 | 0.005 | <0.2, 5 |
|  |  | 378 | 970 | 0.40 | 190 × 10$^3$ |

$^a$Experimental error: 10%.
$^b$Experimental error: 5%.

This example demonstrates that SiNCs are a viable scaffold for very efficient light harvesting antenna. The molecular antennae greatly increases the molar absorption coefficient of SiNCs, thus increasing the overall brightness of the nanocrystal luminescence. This method may be applied to chromophores absorbing across the visible spectrum, especially those with absorption close to the emission peak wavelength of the nanocrystals.

Example 2: Silicone Nanoparticles Functionalized with Tethered Pyrene Units

Synthesis of 1-((Undec-10-Enyloxy)Methyl)Pyrene.

To a mixture of 1-pyrenemethanol (1.00 g, 4.30 mmol, 1 eq), 11-bromide-1-undecene (1.504 g, 6.45 mmol, 1.5 eq) in $CH_3CN$ (25 mL) was added sodium hydride (0.124 g, 5.16 mmol, 1.2 eq) at 80° C. The reaction mixture was stirred vigorously for 48 h at 70° C. After completion of the reaction, three drops of $H_2O$ were added to quench the reaction. The mixture was extracted (3×5 mL) with chloroform. The chloroform layer was dried over $MgSO_4$ and the solvent was removed under reduced pressure to give the solid crude product. The resulting residue was purified by silica column chromatography (hexane/AcOEt 8:2), to give the product as a yellow solid (yield=80%).

$^1$H-NMR (400 MHz, $CDCl_3$) δ: 8.41 (d, J=9.2 Hz, 1H); 8.24-8.20 (m, 2H); 8.19-8.14 (m, 2H); 8.10-8.04 (m, 4H); 6.02-6.04 (m, 1H); 5.23 (s, 2H); 5.08 (d, J=17.2 Hz, 1H); 5.03 (d, J=10.4, 1H); 3.64 (t, J=6.4 Hz, 2H); 2.13-2.07 (m, 2H); 1.75-1.69 (m, 2H); 1.42-1.40 (m, 4H); 1.53-1.30 (m, 8H).

$^{13}$C-NMR (100 MHz, $CDCl_3$) δ: 139.0, 131.7; 131.1; 131.0; 130.6; 129.1; 127.3; 127.2; 127.0; 126.6; 125.6; 124.9; 124.7; 124.6; 124.2; 123.3; 114.0; 71.2; 70.3; 33.7; 29.7; 29.4; 29.3; 29.0; 28.2; 26.1. ESI-MS: 407 [$M^+Na$]; 215 [$M^-C_{11}H_2O$]$^+$.

Figures 16A, 16B:
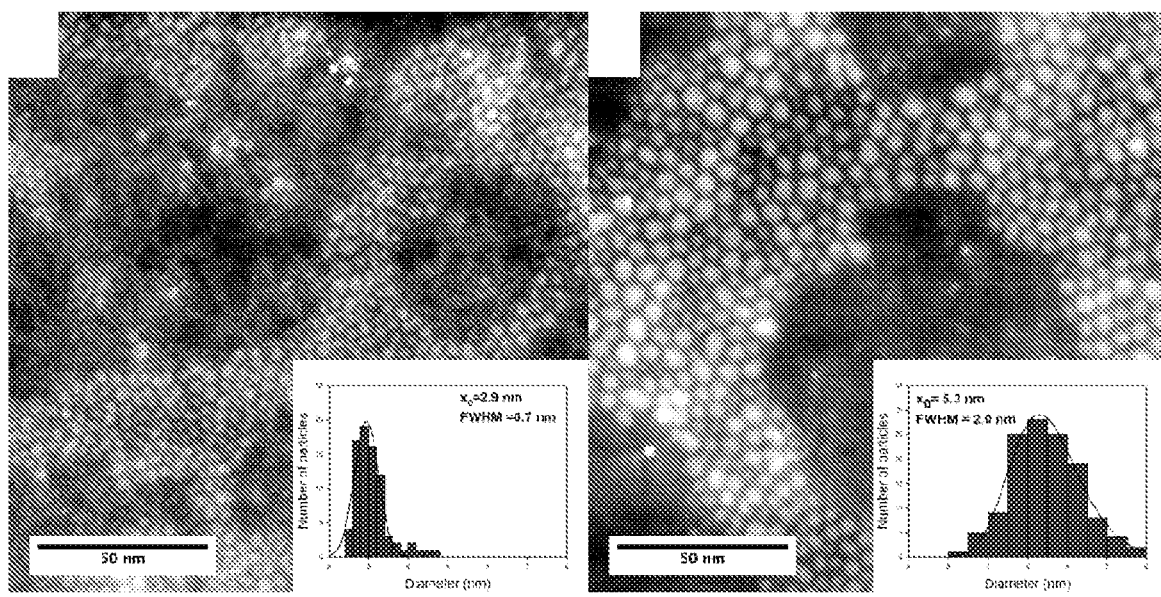
FIG. 16A and FIG. 16B are STEM-HAADF micrographs of two families of SiNC($C_{11}$)Py nanocrystals, with nominal diameters of 3 nm (FIG. 16A) and 5 nm (FIG. 16B). In the inset the size distribution histograms are obtained by manually measuring the size of the nanocrystals. Histograms are fitted with a Lognormal distribution, and the mean value and the FWHM of the distributions, of 2.9 and 5.3 nm respectively, are reported.
Figures 17A, 17B:
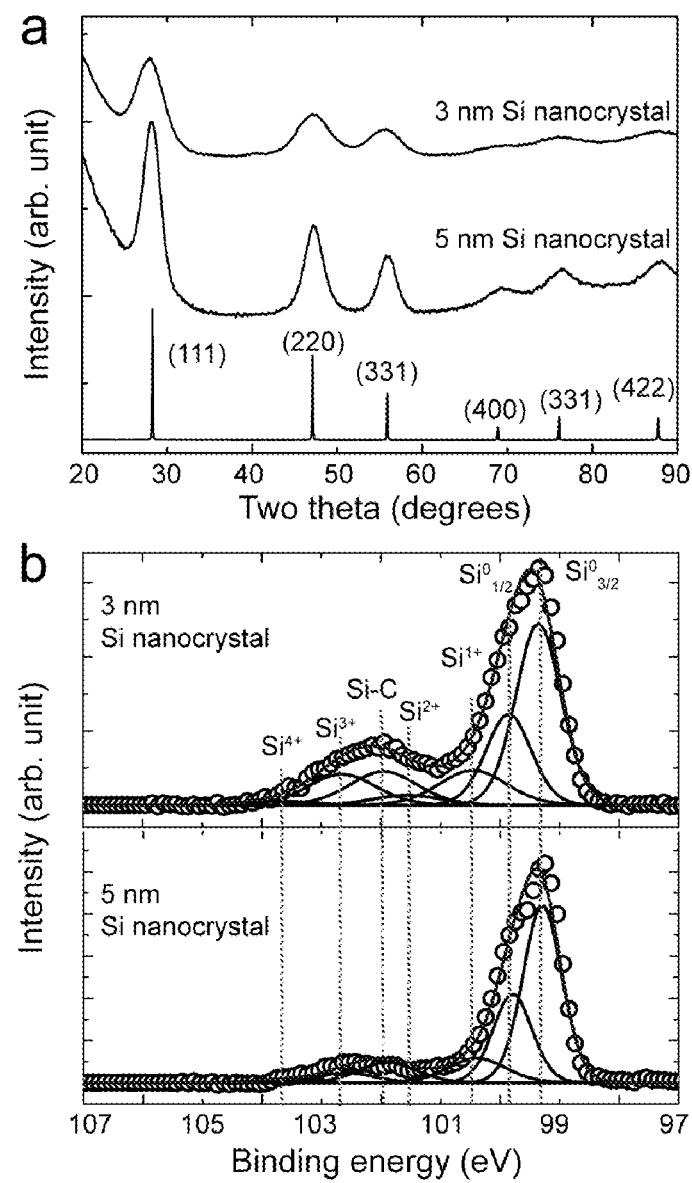
FIG. 17A is an XRD (λ=0.154 nm)
FIG. 17B is an XPS of 3 and 5 nm diameter Si nanocrystals. A reference diffraction pattern is provided for diamond cubic Si in FIG. 17A (PDF #027-1402, a=b=c=5.43088 Å).
Figures 18A, 18B:
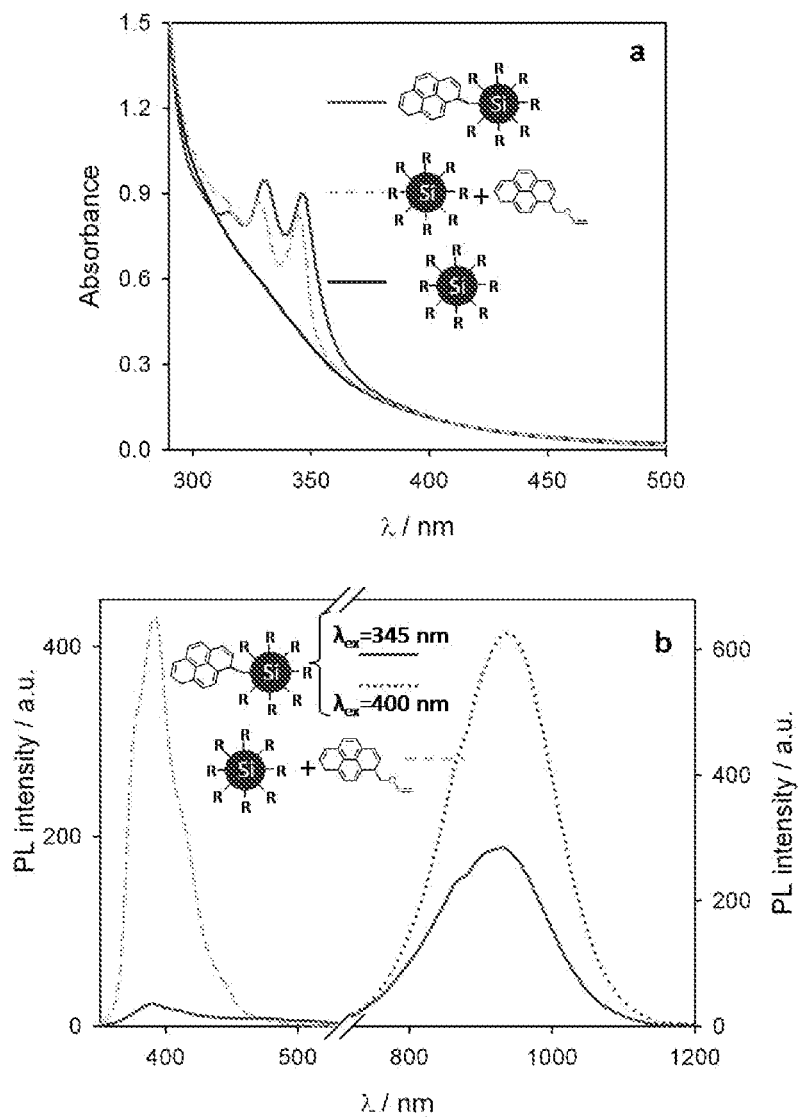
FIG. 18A and FIG. 18B are the absorption (FIG. 18A) and PL spectra (FIG. 18B) of 5 nm diameter SiNC (black line) and SiNC($C_{11}$)Py (solid grey line) in air-equilibrated toluene. PL spectra were recorded for SiNC($C_{11}$)Py with two different excitation wavelengths (solid grey line, $\lambda_{ex}$=345 nm; dotted grey line, $\lambda_{ex}$=400 nm) to photoexcite either the pyrene or SiNCs, respectively. The measurements were made with the dispersion concentration adjusted to optically match the amount of absorbed light under each excitation condition. For comparison, the absorbance and PL spectra for a mixture of SiNC and Py in the proper ratio is shown in dashed light grey line ($\lambda_{ex}$=345 nm).

Hydride-terminated SiNCs were obtained via thermal disproportionation of commercially available HSQ followed by chemical etching with a solution of HF and HCl to remove the oxide matrix, as described in Example 1. The SiNCs were treated by thermal hydrosilylation with either 1-dodecene or a combination of 1-dodecene and pyrene chromophore (Py). Two different alkyl tether lengths ($C_{11}$ and $C_3$) and two different Si core diameters were used. The nanocrystals were synthesized at either 1100° C. or 1200° C. at a heating rate of 18° C./min and held at that temperature for an hour under reducing atmosphere (93% $N_2$, 7% $H_2$). The SiNC/$SiO_2$ composite were etched with 48% HF and 37.5% HCl (10:1 v/v) in the dark for 4-6 hours and then centrifuged at 8000 rpm for 5 min. The H-terminated SiNCs were then rinsed once with deionized (DI) water, twice with ethanol, and once with chloroform. These nanocrystals had average diameters determined by TEM of 2.9±0.7 nm and 5.3±2.0 nm, respectively (FIG. 16A and FIG. 16B). These are referred to as 3 nm and 5 nm SiNCs. X-ray diffraction of these nanocrystals is characteristic of diamond cubic Si (PDF #027-1402, a=b=c=5.43088 Å). X-ray photoelectron spectroscopy (XPS) confirms the formation of Si—C bonds on the nanocrystals surface with limited surface oxidation (FIG. 17A and FIG. 17B).

The nanocrystals were dispersed in 5 mL of 1-dodecene with 490 mg of 1-(allyloxymethyl)pyrene (1:12 pyrene:dodecene molar ratio) to obtain SiNC($C_3$)Py sample, in 5 mL of 1-dodecene to have SiNC and 4 mL of 1-dodecene with 250 mg of 1-((undec-10-en-1-yloxy)methyl)pyrene (1:27 pyrene:dodecene molar ratio) for SiNC($C_{11}$)Py. The initially turbid dispersions are put through three freeze-pump-thaw cycles, and then heated to 170° C. under $N_2$ flow for 12 hours. Over time, the dispersions became optically clear, indicating that passivation of Si nanocrystals had occurred. To purify the nanocrystals, the solutions were transferred to a glass centrifuge tube, spin at 8000 rpm for 5 min and discard the precipitate (poorly capped SiNCs) on the bottom. The supernatant was transferred to another glass centrifuge tube and underwent many centrifugation/precipitation cycles using toluene/ethanol solvent/antisolvent pair. The final SiNC, SiNC($C_3$)Py, SiNC($C_{11}$)Py samples were dispersed in toluene at a concentration of 3-5 mg/mL.

Figure 9:
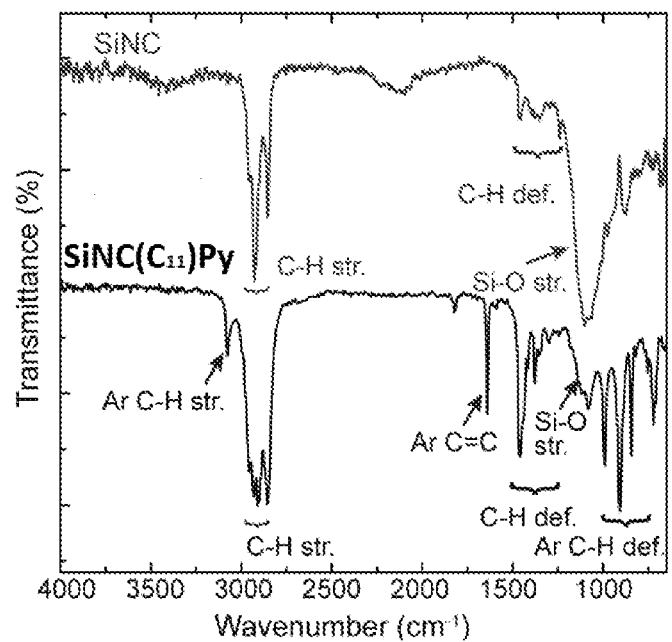
FIG. 9 is the FTIR spectra of SiNC and SiNC($C_{11}$)Py of 3 nm diameter.

The FTIR spectrum of SiNC (FIG. 9) shows features due to ν(C—H) stretching at 3000-2850 cm$^{-1}$ and δ(C—H) bending at 1500-1350 cm$^{-1}$; the presence of the oxygen is evidenced by the strong ν(Si—O) stretching at 1024 cm$^{-1}$. For SiNC($C_{11}$)Py the covalent attachment of the ligand to the surface is confirmed by the presence of aromatic ν(C—H) stretching at 3100-2890 cm$^{-1}$, ν(C=C) stretching at 1640 cm$^{-1}$ and δ(C—H) bending at 1480 cm$^{-1}$ and 940-800 cm$^{-1}$. There is no evidence of ν(Si—H) (ca. 2100 cm$^{-1}$) consistent with effective functionalization.

The optical properties (Table 2) of SiNC($C_{11}$)Py dispersed in toluene at room temperature were compared to those of the corresponding alkyl functionalized nanocrystals (SiNC) and to those of SiNC($C_3$)Py.

Figure 10:
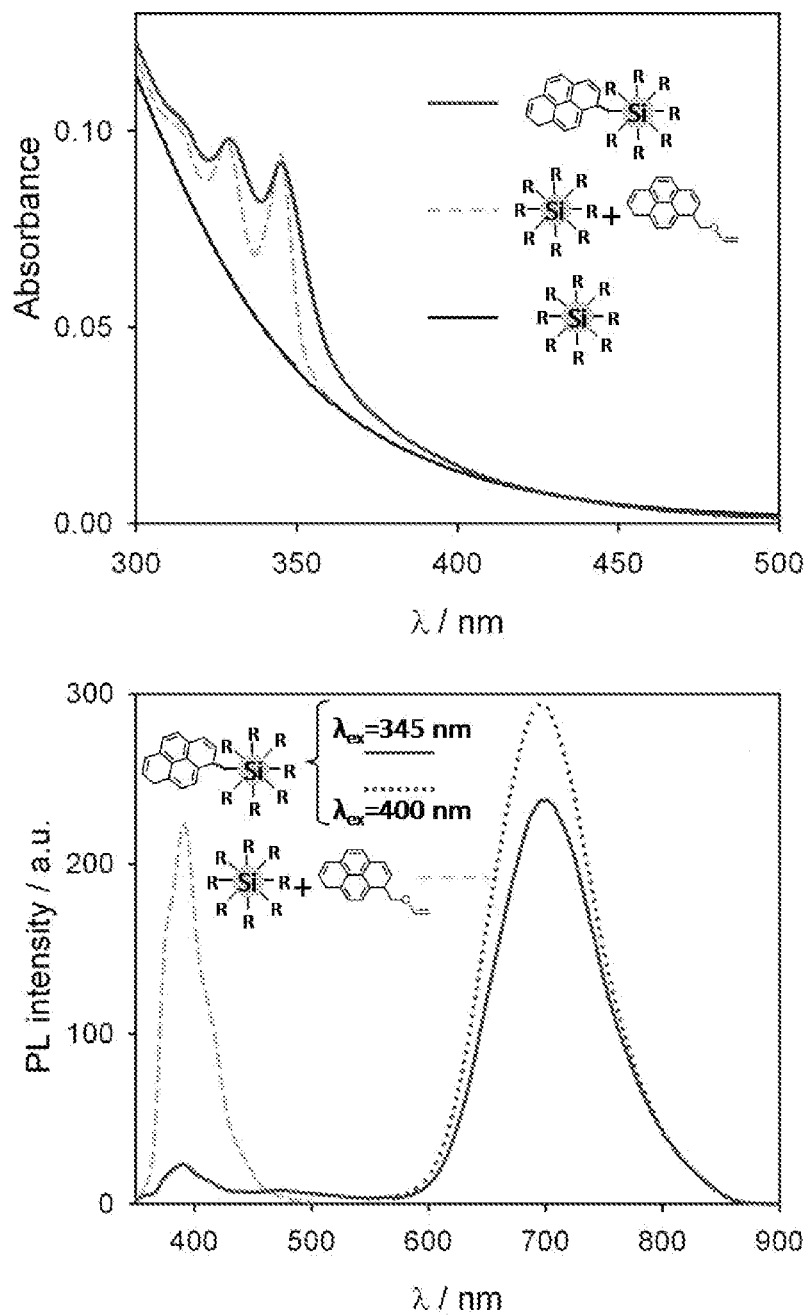
FIG. 10 shows the absorption (top) and PL spectra (bottom) of 3 nm diameter SiNC (black line) and SiNC($C_{11}$)Py (solid grey line) in air-equilibrated toluene. PL spectra were recorded for SiNC($C_{11}$)Py with two different excitation wavelengths (solid grey line, $\lambda_{ex}$=345 nm; dotted grey line, $\lambda_{ex}$=400 nm) to photoexcite either the pyrene or SiNCs, respectively. The measurements were made with the dispersion concentration adjusted to optically match the amount of absorbed light under each excitation condition. For comparison, the absorbance and PL spectra for a mixture of SiNC and Py in the proper ratio is shown in dashed light grey line ($\lambda_{ex}$=345 nm).
Figures 14A, 14B, 14C, 14D:
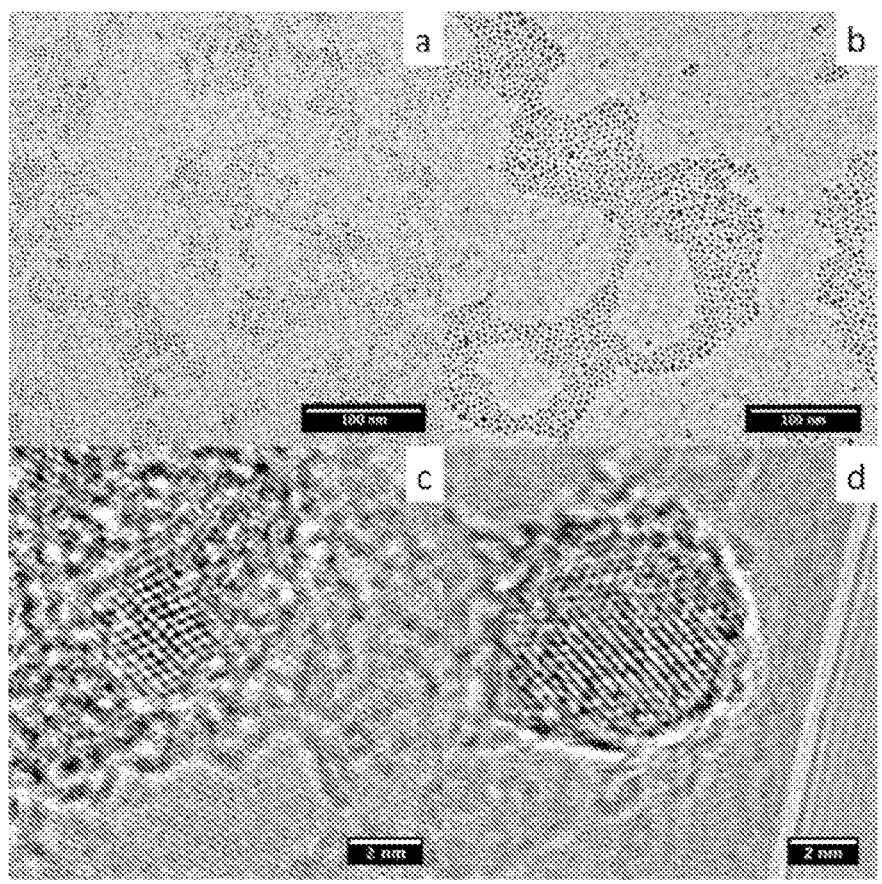
FIG. 14A and FIG. 14B are low magnification TEM micrographs of 3 nm (FIG. 14A) and 5 nm (FIG. 14B) SiNC($C_{11}$)Py deposited on CVD graphene.
FIG. 14C and FIG. 14D are high magnification HRTEM image of a supported on graphene, showing the Si (111) lattice fringes at 0.31 nm.

The absorption spectrum of SiNC($C_{11}$)Py (solid grey line in FIG. 10 (top) and FIG. 14A for 3 and 5 nm diameter, respectively) shows a structured absorption band of the pyrene chromophore superimposed on the unstructured SiNC absorption (SiNC, solid black line). The absorbance maximum for the Py occurs at 345 nm. Based on the molar absorption coefficients of Py ($\varepsilon_{345\ nm}$=4.4×10$^4$ M$^{-1}$cm$^{-1}$) and SiNC ($\varepsilon_{400\ nm}$=5×10$^4$ M$^{-1}$ cm$^{-1}$ and 5.3×10$^5$ M$^{-1}$cm$^{-1}$ for 3 and 5 nm diameter), it is estimated that there are, on average, 3.5 and 50 pyrene chromophores attached to each 3 nm and 5 nm nanocrystal, respectively.

Upon excitation of the pyrene chromophores of SiNC($C_{11}$)Py at 345 nm, a very weak pyrene emission is observed with maximum at 390 nm (solid grey line in FIG. 10 (bottom) and FIG. 14B for 3 and 5 nm diameter, respectively): $\Phi_{PL}$=0.006 compared to 0.06 for Py chromophore in air-equilibrated solution (Table 2), quenching efficiency $\eta_q$=90%. Moreover, the shape of the emission band is different from that of Py:SiNC($C_{11}$)Py display a shoulder at 470 nm, which is typical of an excimer emission.

Figure 19:
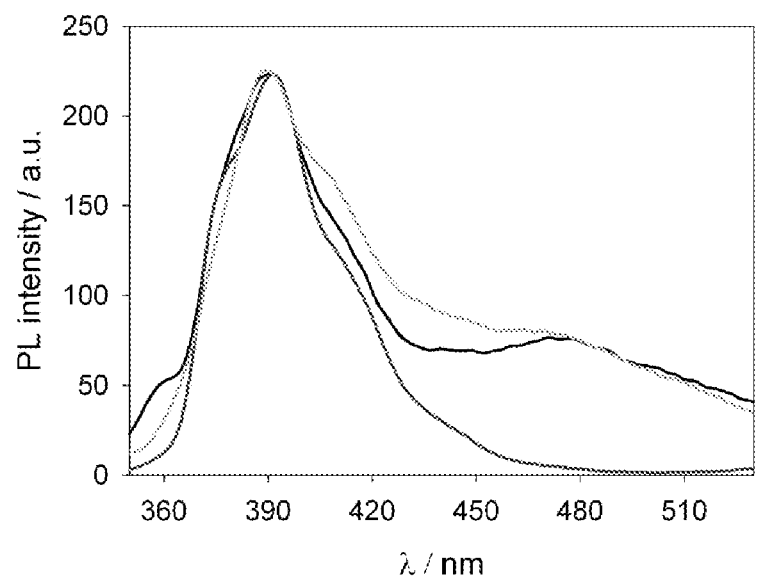
FIG. 19 is a normalized emission spectra of SiNC(C$_3$)Py (dark grey line, d=3 nm) and SiNC(C$_{11}$)Py (d=3 nm, black line; d=5 nm, light grey line) of the pyrene chromophore in toluene solution at room temperature. $\lambda_{ex}$=345 nm.

The pyrene emission intensity decay can be fitted by a double exponential (Table 2), in which the shorter component is assigned to the quenched pyrene monomer, while the longer component to the pyrene excimer. Indeed, the percentage of the longer lifetime increases by recording the emission intensity at 470 nm compared to that at 400 nm. The excimer emission was not present for the shorter chain SiNC($C_3$)Py (FIG. 19). The pyrene chromophores are embedded within the dodecyl ligand layer on the nanocrystals when linked by the shorter $C_3$ tether, which eliminates the interaction between pyrene units; whereas, the longer $C_{11}$ tether places the Py units far enough away from the dodecene monolayer that *Py-Py interactions become possible.

Figure 20A:
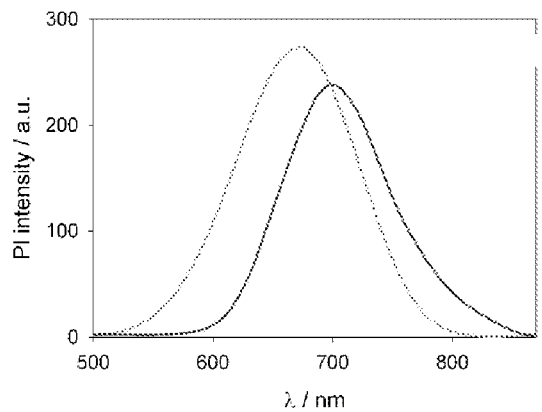
FIG. 20A and FIG. 20B are photoluminescence spectra of SiNC (light grey line) and SiNC(C$_{11}$)Py (dark grey line) of 3 nm (FIG. 20A) and 5 nm (FIG. 20B) dispersed in toluene. The two samples were optically matched at the excitation wavelength of 420 nm.
Figure 20B:
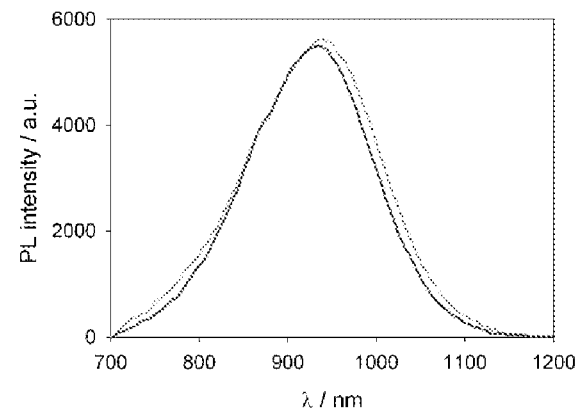

Photoexcitation of the Si core at 400 nm gives rise to similar PL spectra for both the SiNC($C_{11}$)Py and SiNC. Py does not absorb any light at this wavelength. In particular, for the 3 nm SiNC($C_{11}$)Py a slight decrease of the emission quantum yield (13% compared to 16% for SiNC, Table 2) is accompanied by a red shift of the emission maximum (FIG. 20A). No difference in the luminescent decay was observed in argon-purged toluene, indicating that dioxygen does not quench the SiNC emission.

To evaluate the sensitized emission of the Si core by pyrene, the emission intensity of the silicon core ($\lambda_{max}$=700 nm and 970 nm for 3 and 5 nm diameter SiNCs) recorded for two optically matched solutions of SiNC($C_{11}$)Py at the excitation wavelengths of 345 nm, where 50% of the light is absorbed by pyrene units for both 3 nm and 5 nm diameter, and 420 nm, where 100% of light is absorbed by the silicon core, were compared. The sensitization is higher in the case of SiNC($C_{11}$)Py of 3 nm diameter ($\eta_{sens}$=70%) compared to the 5-nm nanocrystals ($\eta_{sens}$=30%, Table 1). These results are confirmed by the excitation spectra (see e.g., FIG. 21) performed at $\lambda_{em}$=690 nm. Upon excitation at 345 nm the 3-nm SiNC($C_{11}$)Py shows a brightness of 140% compared to the 3-nm SiNCs.

The sensitization efficiency is lower than that observed for the SiNC($C_3$)Py (Table 2) because of the longer average distance between pyrene and Si core which slows down the energy transfer process. On the other hand, the quenching efficiency of pyrene is only slightly lower than in SiNC($C_3$)Py because in the case of SiNC($C_{11}$)Py, the radiative decay of the fluorescent pyrene monomer excited state competes, not only with the energy transfer process, but also with excimer formation.

TABLE 2

Photophysical properties of SiNC, SiNC($C_{11}$)Py and SiNC($C_3$)Py dispersed in air-equilibrated toluene at 298 K. For comparison, the properties of the model compound Py are also reported. The quenching efficiency of the pyrene emission ($\eta_q$) and the sensitization efficiency of the Si core emission ($\eta_{sens}$) are presented.

| | diameter [nm] | $\lambda_{ex}$ [nm] | $\lambda_{PL}$ [nm] | $\Phi_{PL}$ | $\tau$ [ns] | $\eta_q$ | $\eta_{sens}$ |
|---|---|---|---|---|---|---|---|
| SiNC | 3 | 420 | 635 | 0.16$^a$ | 70 × 10$^3$ | — | — |
| SiNC($C_{11}$)Py | 3 | 345 | 400 | 0.006 | 2.0, 11 | 90% | 70% |
| | | 420 | 700 | 0.13 | 90 × 10$^3$ | | |
| SiNC($C_3$)Py | 3 | 345 | 400 | 0.005 | <0.2, 5 | >95% | >95% |
| | | 420 | 690 | 0.11$^a$ | 95 × 10$^3$ | | |
| Py | — | 345 | 400 | 0.06 | 18 | — | — |
| SiNC | 5 | 420 | 970 | 0.45 | 150 × 10$^3$ | — | — |
| SiNC($C_{11}$)Py | 5 | 345 | 400 | 0.006 | 3.2, 12 | 90% | 30% |
| | | 420 | 940 | 0.42 | 160 × 10$^3$ | | |
| SiNC($C_3$)Py | 5 | 345 | 400 | 0.005 | <0.2, 5 | >90% | 65% |
| | | 420 | 970 | 0.40 | 190 × 10$^3$ | | |

$^a$These values are higher than those reported in Example 1 since the PL quantum yield of the standard was changed from 0.028 to 0.040 (Suzuki, et al., *Phys. Chem. Chem. Phys.* 2009, 11:9850-9860).

Example 3: Interaction of Silicon Nanocrystals with Carbon-Based Materials

When the tether length is long enough to allow the Py units to extend away from the dodecene passivation layer into the solution, it provides the possibility for Py interactions with other molecules and surfaces in the surrounding environment. This is not the case when the Py units are buried in the ligand passivation layer. The observation of excimer formation for the long-tether SiNC($C_{11}$)Py units indicates that the Py is exposed significantly to the surroundings. Pyrene interacts strongly with carbon allotropes like carbon nanotubes and graphene by π-π stacking (An, et al. *Nano Lett.* 2010, 10:4295-4301; Schlierf, et al. *Nanoscale* 2013, 5:4205-4216). A series of experiments exposing SiNC ($C_{11}$)Py to $C_{60}$, carbon nanotubes, and graphene were carried out.

Figures 11A, 11B, 11C:
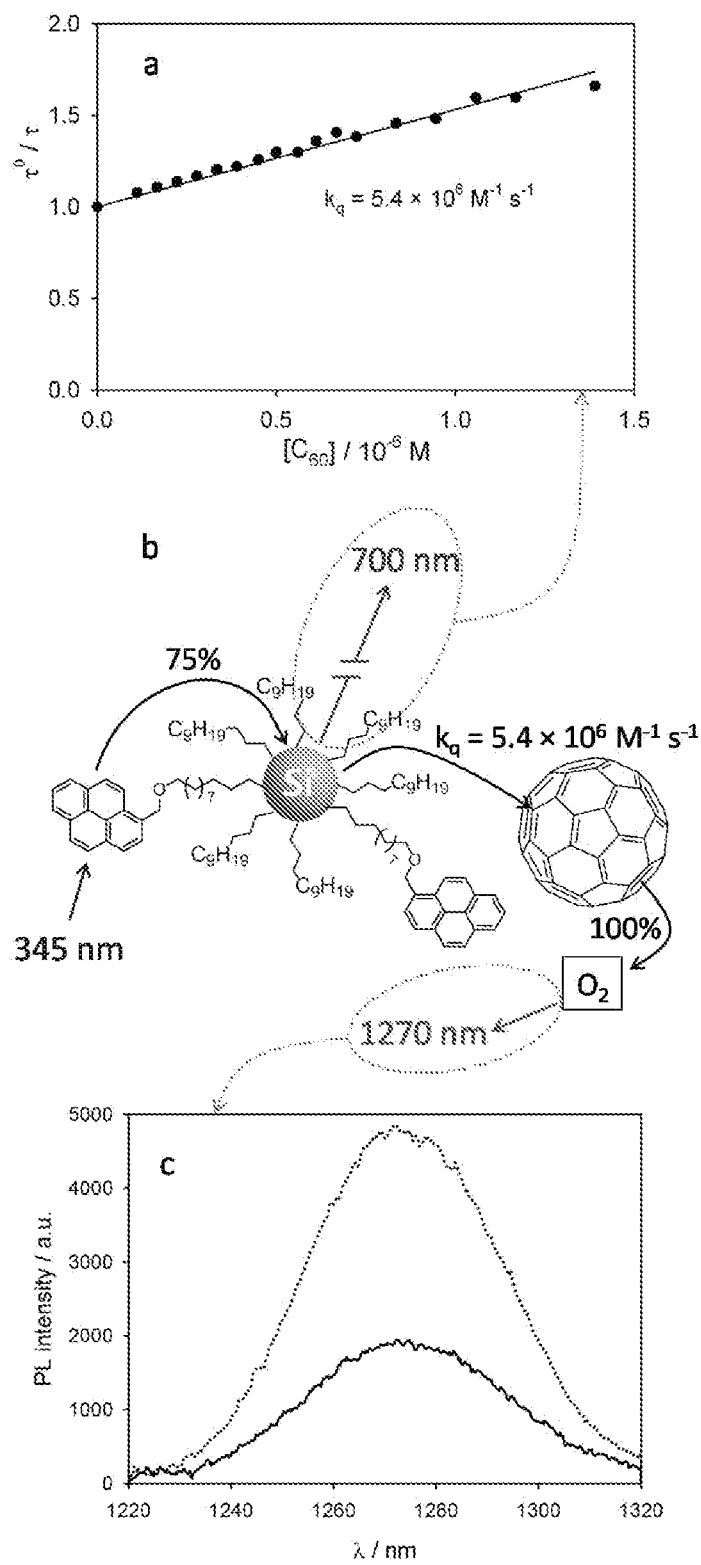
FIGS. 11A-11C show the quenching process occurring for SiNC($C_{11}$)Py (diameter 3 nm) dispersed in air-equilibrated toluene in presence of $C_{60}$.
Figure 22:
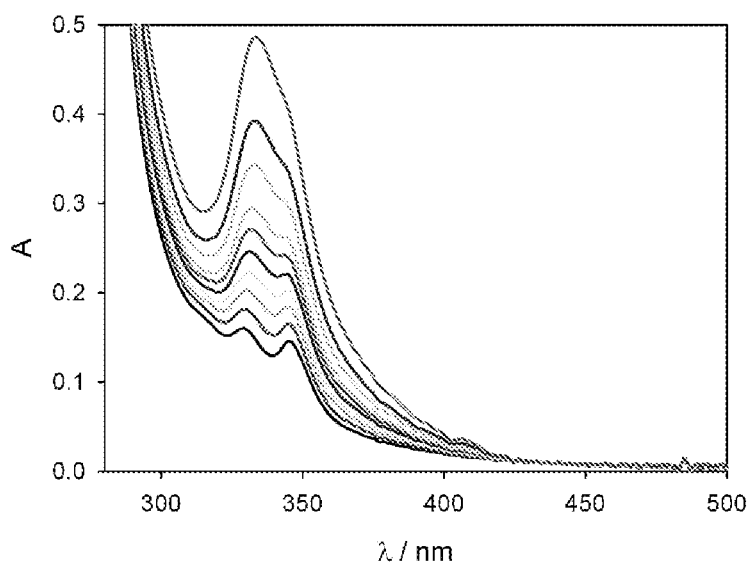
FIG. 22 is a spectrophotometric titration of 3 nm diameter SiNC(C$_{11}$)Py dispersed in air-equilibrated toluene (solid black line) with C$_{60}$ (up to 7×10$^{-6}$M).
Figure 25:
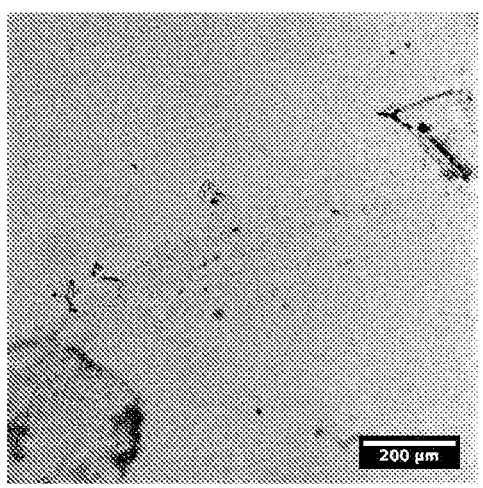
FIG. 25 is an optical microscope image of a graphene flake on a quartz slide.

$C_{60}$ was added to a dispersion of 3 nm SiNC($C_{11}$)Py in air-equilibrated toluene. The absorption spectra (FIG. 22) are the mere superposition of the SiNC($C_{11}$)Py and that of $C_{60}$, showing no evidence of ground state interaction (Hwang, et al. *Fuller. Sci. Technol.* 1999, 7:437-454). Photoexcitation at 345 nm induces predominantly pyrene light absorption, but due to energy transfer, the PL spectrum is dominated by the Si nanocrystals band at 700 nm. The addition of $C_{60}$ led to a decrease in Si nanocrystal PL and a concomitant decrease of the lifetime. FIG. 11A shows a Stern-Volmer plot of the ratio of the lifetimes in the absence ($\tau_0$) and presence of $C_{60}$ ($\tau$) as a function of $C_{60}$ concentration.

This plot is linear, suggesting a dynamic quenching process (Equation 1): SiNC($C_{11}$)Py interacts with $C_{60}$ only in the excited state and not in the ground state, in agreement with the spectrophotometric titration.

$$\tau^0/\tau = 1 + k_q \tau^0 [C_{60}] \qquad (1)$$

From this equation, the quenching constant ($k_q$) can be evaluated: $k_q = 5.4 \times 10^6 M^{-1} s^{-1}$.

In order to understand the mechanism of quenching, the sensitization of the lowest-energy triplet excited state of $C_{60}$ ($^3C_{60}$) was investigated through an excitation of the silicon nanocrystals. The transient absorption spectrum of $^3C_{60}$ with a maximum at 730 nm (Sension, et al. *J. Phys. Chem.* 1991, 95:6075-6078; Accorsi, et al. *J. Phys. Chem. C* 2010, 114:1385-1403; Guldi, et al. *Acc. Chem. Res.* 2000, 33:695-703) is superimposed on the transient spectrum deriving from the silicon nanocrystals (FIG. 23A and FIG. 23B), so the population of $^3C_{60}$ was probed by monitoring the sensitized emission from the lowest-energy singlet excited state of dioxygen $^1O_2$ (FIG. 11B). It is known that $^3C_{60}$ sensitizes with unitary efficiency the population of $^1O_2$ (Hung, et al. *J. Phys. Chem.* 1991, 95:6073-6075; Rio, et al. *Tetrahedron* 2003, 59:3833-3844) that radiatively deactivates with a maximum at 1270 nm. FIG. 11C reports the emission band of $^1O_2$ obtained for SiNC($C_{11}$)Py dispersed in toluene upon the addition of $C_{60}$ (1.5×10$^{-5}$M) exciting at 420 nm, where light is selectively absorbed by the nanocrystals, compared to that of $C_{60}$ in toluene upon excitation at 350 nm for optically matched solutions at the excitation wavelength. Some interesting results are the following: (i) SiNC($C_{11}$)Py, as well as SiNC, do not sensitize $^1O_2$ emission, in agreement with the lack of sensitivity to dioxygen of the emission quantum yields of the silicon nanocrystals; (ii) upon addition of $C_{60}$ (1.5×10$^{-5}$M) to SiNC($C_{11}$)Py, the silicon nanocrystal emission is quenched with an efficiency of ca. 85% and (iii) a concomitant sensitization of $^1O_2$ emission takes place with efficiency of ca. 40%, as evaluated by the comparison of the emission intensity obtained for the sample containing only $C_{60}$. This result demonstrates that energy transfer from the silicon core to $C_{60}$ takes place.

To evaluate the occurrence of a concomitant photoinduced electron transfer between SiNC($C_{11}$)Py and $C_{60}$, transient absorption spectra in the NIR region were registered, but no signal of $C_{60}^-$ ($\lambda_{max}$=1080 nm) (Nojiri, et al. *J. Phys. Chem. A* 1998, 102:5215-5219) was detected. It is worth noting that the silicon nanocrystals have a transient absorption spectrum extending to the NIR, so the formation of a small amount of $C_{60}^-$ under the experimental conditions cannot be excluded.

The transient absorption spectrum of the luminescent state of SiNC($C_{11}$)Py (diameter 3 nm, FIG. 21, solid grey line) in degassed toluene upon excitation at 532 nm is superimposed to the transient absorption spectrum of the lowest triplet excited state of $C_{60}$ (FIG. 21, light grey line) under the same experimental condition. Moreover, also in the NIR spectral region between 800 and 1200 nm, the SiNC($C_{11}$)Py (diameter 3 nm) shows a broad signal which prevents the observation of the radical anion of $C_{60}$. This result precludes the possibility of investigating energy and electron transfer processes by this technique.

Figure 21:
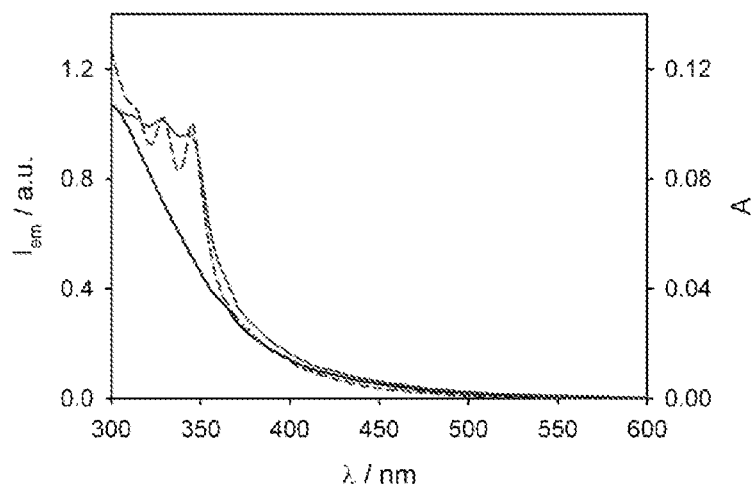
FIG. 21 is the excitation spectra of 3 nm diameter SiNC(C$_{11}$)Py (solid grey line) and SiNC (solid black line) recorded with $\lambda_{em}$=690 nm. For comparison purposes, the absorption spectrum of SiNC(C$_{11}$)Py is reported (grey dashed line).

The absorption decay of SiNC($C_{11}$)Py (FIG. 21, dark grey line) matches the corresponding emission decay (lifetime reported in Table 2). Upon addition of $C_{60}$ (1.5×10$^{-5}$M), the emission intensity shows a much faster decay (FIG. 21, black dashed line) in agreement with a 75% quenching estimated by steady-state emission spectroscopy. On the other hand, the transient absorption decay of the same solution at 735 nm is dominated by the $C_{60}$, as evidenced by the match with the decay of a $C_{60}$ solution (FIG. 21, light grey line).

Figures 12A, 12B:
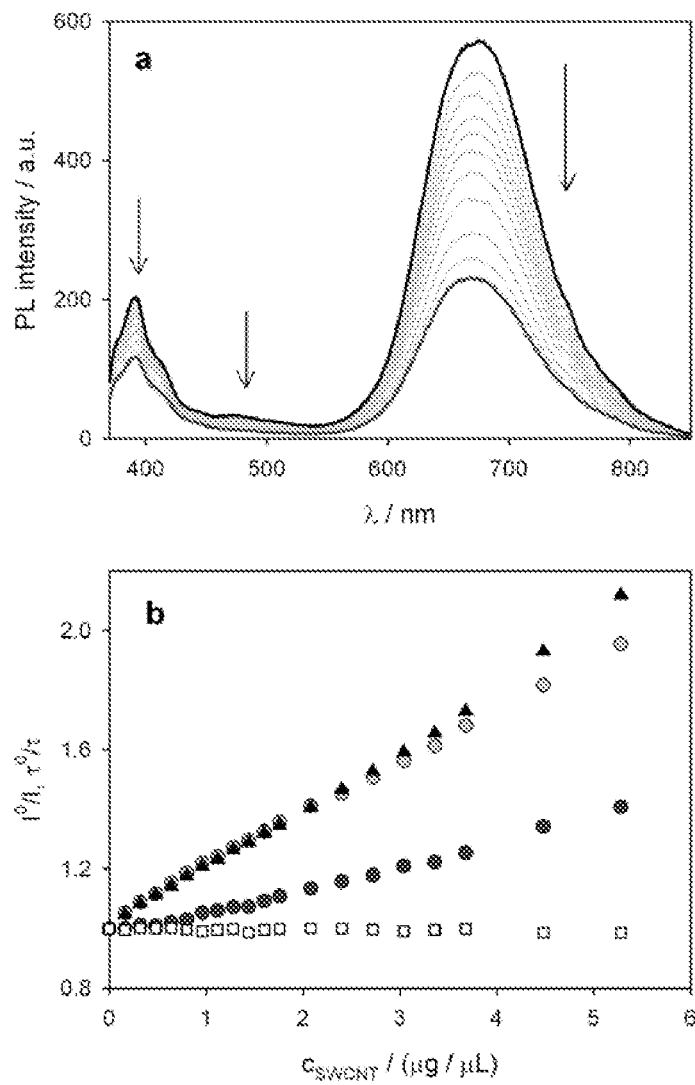
FIG. 12A is the PL spectra of SiNC($C_{11}$)Py ($\lambda_{ex}$=345 nm) upon addition of an increasing amount of a 40 μg/ml solution of SWCNT in dichloromethane.
FIG. 12B shows the ratio of PL intensities at 390 nm (dark grey circles), 470 nm (light grey circles) and 700 nm (black triangles), as well as silicon nanocrystals lifetimes (empty squares) in the absence ($I^0$, $\tau^0$) and presence (I, τ) of increasing amounts of SWCNTs.

Upon addition of single-walled carbon nanotubes (SW-CNTs) to a sample of SiNC($C_{11}$)Py (3-nm diameter) in air-equilibrated toluene, the emission intensity of the silicon core at 700 nm (FIG. 12A) decreases (after correction for the light absorbed and scattered by the SWCNT at the excitation wavelength) with no change of the corresponding lifetime. This result is in line with a static quenching, in which the SiNC($C_{11}$)Py and SWCNTs are associated in the ground state thanks to π-π stacking, as previously reported for pyrene and CNTs (Chen, et al. *J. Am. Chem. Soc.* 2001, 123:3838-3839). The addition of SWCNTs causes quenching also of the pyrene emission. This result is indicative of an interaction of the pyrene unit with the carbon nanotube, creating a competitive path to the excimer formation. In particular, the excimer emission band at 470 nm is quenched with the same slope as the silicon nanocrystal emission, while the pyrene monomer emission band at 390 nm is quenched to a lower degree. This experimental finding is consistent with the fact that two opposite mechanisms are active: the pyrene emission is quenched by an interaction with the carbon nanotube, but it is revived by the suppression of the excimer formation.

Figure 13:
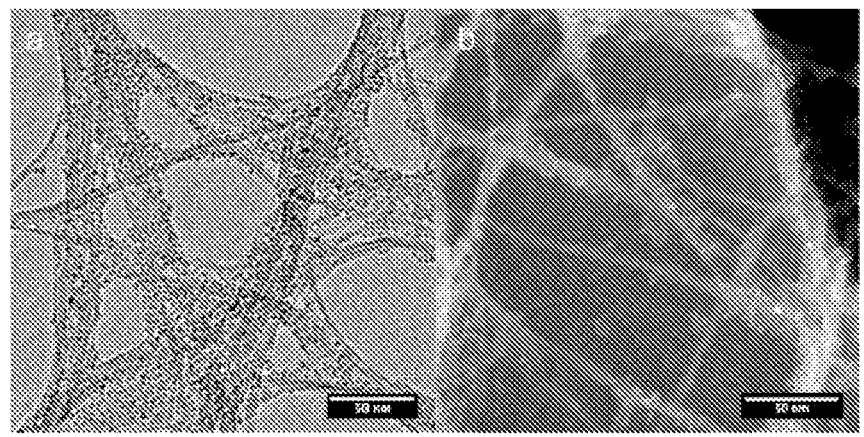
FIG. 13 shows a TEM micrograph (left) and STEM-HAADF micrograph (right) of SWCNTs coated by SiNC ($C_{11}$)Py.

Further confirmation of the ground state interaction is provided by TEM of the adduct formed by SWCNTs and SiNC($C_{11}$)Py. The HRTEM and STEM-HAADF micrographs (FIG. 13) highlight that nanocrystals are preferentially located on the SWCNTs rather than on the carbon film coated copper grid.

To test the interaction of SiNC($C_{11}$)Py with graphene, it was not possible to study the solution phase behavior because of the lack of dispersibility of exfoliated graphene in a solvent suitable for SiNC($C_{11}$)Py. Therefore, a graphene film grown by Chemical Vapor Deposition (CVD) (Ortolani, et al. *Nano Lett.* 2012, 12:5207-5212) in a solution of the nanocrystal was studied. The TEM grids were prepared by transferring CVD graphene onto Cu Quantifoil R2/1 grids and dipping the grid into SiNCs solution. SEM samples were prepared by partially covering a Si/SiO$_2$ p+ wafer (320 nm SiO$_2$) with a CVD graphene membrane, then the SiNCs were spin coated on the top of the graphene/SiO$_2$ side. The same method was used for the photoluminescence and wide-field luminescence microscopy were performed by replacing the Si/SiO$_2$ wafer with an UV transparent quartz slide. The nanocrystals (FIGS. 14A-14D) formed a uniformly dispersed monolayer of nanoparticles, without the formation of thick aggregates. The very low thickness of the graphene film, between 1 and 3 layers, allowed deeper insight on the crystalline structure of the nanoparticles by enhancing the contrast for a light element such as silicon, as previously reported by Panthani, et al. *J. Phys. Chem. C* 2012, 116:22463-22468.

Figures 15A, 15B:
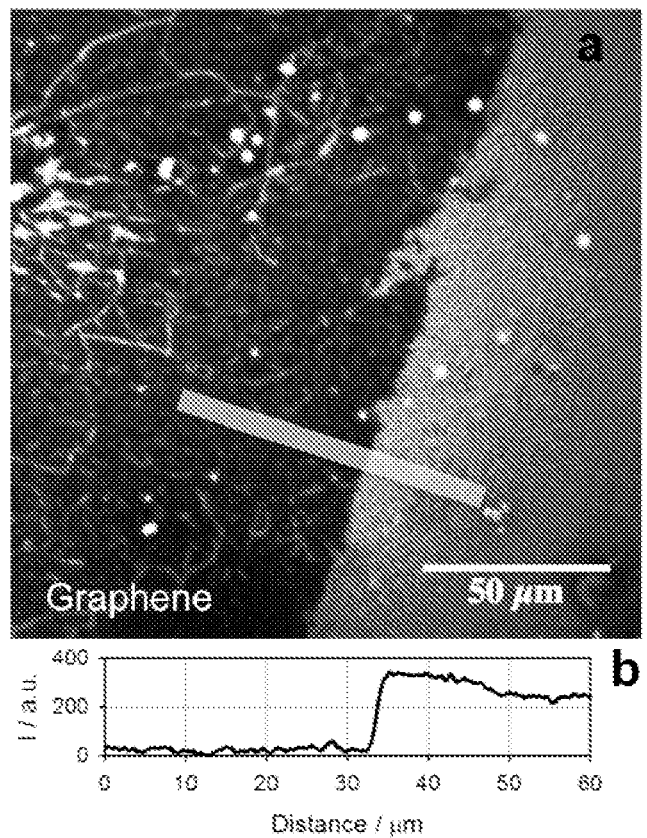
FIG. 15A is a wide-field luminescence microscope image of SiNC($C_{11}$)Py (3 nm diameter) deposited on quartz and graphene coated quartz. The image shows the graphene film edge.
FIG. 15B is an emission intensity profile registered by wide-field luminescence microscopy along the white line in FIG. 15A.

The emission of SiNC($C_{11}$)Py (3 nm diameter) is significantly lower in intensity on the graphene layer, as evidenced by both the PL spectrum and the wide-field luminescence image reported in FIG. 15A and FIG. 15B. The wide-field image shows luminescent stripes on the graphene that are likely due to breaks in the graphene films. SEM images of SiNC($C_{11}$)Py with diameter of 5 nm (FIG. 24A and FIG. 24B, the smallest particles are not visible by SEM) on quartz slides partially covered by CVD graphene show a uniform distribution of the nanocrystals on graphene and quartz. Therefore, the different emission intensity registered on quartz and graphene is not due to a different distribution on the two substrates, but it is ascribed to a quenching mechanism. The luminescence lifetimes registered on quartz and graphene are similar, as expected for a static quenching. The most likely quenching mechanism is energy transfer, as previously reported for CdSe quantum dots (Chen, et al. *ACS Nano* 2010, 4:2964-2968).

Tethers that are long enough for the pyrene to extend beyond the capping ligand layer into the surrounding solution allow association with molecules and substrates in the surroundings, such as the carbon allotropes. TEM analysis shows the interaction of SiNCs with SWCNTs and graphene. The detailed study of this interaction by spectroscopical techniques elucidates the occurrence of quenching processes. Energy transfer process can occur either to or from the Si nanocrystals. Energy is transferred from the organic chromophore to the silicon core in the case of pyrene; whereas, energy flows from the quantum dots to nearby fullerenes to populate their lowest energy triplet excited state. This means that electronic energy harvested by the hybrid SiNC($C_{11}$)Py material can be further exploited by an interaction with external systems.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A photoactive particle comprising:
   a pyrene luminescent chromophore covalently bonded to a silicon nanocrystal, wherein the photoactive particle exhibits an absorption spectrum including a first wavelength and a photoluminescence emission spectrum for excitation at the first wavelength, and wherein the photoactive particle exhibits an external photoluminescence quantum yield of at least 10%, wherein the external photoluminescence quantum yield corresponds to a number of photoluminescent photons emitted by the photoactive particle per incident photon having a wavelength in the absorption spectrum.

2. The photoactive particle of claim 1, wherein from 1 to 100 pyrene luminescent chromophores are covalently bonded to the silicon nanocrystal.

3. The photoactive particle of claim 1, wherein the pyrene luminescent chromophore is biocompatible.

4. The photoactive particle of claim 1, wherein the first wavelength corresponds to electromagnetic radiation having the first wavelength.

5. The photoactive particle of claim 1, wherein the pyrene luminescent chromophore comprises pyrene or a pyrene derivative.

6. The photoactive particle of claim 1, wherein the silicon nanocrystal is biocompatible.

7. The photoactive particle of claim 1, wherein the silicon nanocrystal is linked to the pyrene luminescent chromophore by a C1-C50 alkyl, alkenyl, or alkynyl linker.

8. The photoactive particle of claim 1, wherein the silicon nanocrystal is linked to the pyrene luminescent chromophore by a C1-C8 alkyl group.

9. The photoactive particle of claim 1, wherein the silicon nanocrystal is linked to the pyrene luminescent chromophore by a C8-C20 alkyl group.

10. The photoactive particle of claim 1, wherein the silicon nanocrystal is from 1 to 10 nm in diameter.

11. The photoactive particle of claim 1, wherein the photoactive particle exhibits a molar absorption coefficient at the first wavelength of from about $4.4 \times 10^4 M^{-1} cm^{-1}$ to about $15.9 \times 10^5 M^{-1} cm^{-1}$.

12. The photoactive particle of claim 1, wherein the external photoluminescence quantum yield is at least double an external photoluminescence quantum yield of the silicon nanocrystal only.

13. The photoactive particle of claim 1, wherein the first wavelength is from 345 nm to 378 nm.

14. The photoactive particle of claim 1, wherein the photoluminescence emission spectrum includes wavelengths of from 400 to 970 nm.

15. The photoactive particle of claim 1, wherein the photoactive particle exhibits a brightness intensity of from $4.4 \times 10^3 M^{-1} cm^{-1}$ to $6.36 \times 10^5 M^{-1} cm^{-1}$.

16. The photoactive particle of claim 1, wherein the photoactive particle exhibits an absorbance 300% more or greater than the silicon nanocrystal only.

17. The photoactive particle of claim 1, wherein the photoactive particle exhibits a luminescent excited state lifetime of from 50 µs to 190 µs.

18. The photoactive particle of claim 1, wherein a brightness intensity of the photoactive particle is 300% more or greater than the silicon nanocrystal only.

19. The photoactive particle of claim 1, a cell recognition moiety bonded to the silicon nanocrystal, wherein the cell recognition moiety is selected from the group consisting of a receptor, ligand, polynucleotide, peptide, polynucleotide binding agent, antigen, antibody, or combinations thereof.

20. The system A mixture comprising the photoactive particle of claim 1 and a carbon allotrope.

21. A composition comprising, a plurality of the photoactive particles according to claim 1.

22. A pharmaceutical composition, comprising:
the photoactive particle according to claim 1, and
a pharmaceutically acceptable excipient.

23. A method of making the photoactive particle according to claim 1, comprising
providing a silicon nanocrystal,
providing a solution of the pyrene luminescent chromophore configured to covalently link to the silicon nanocrystal,
dispersing the silicon nanocrystal in the solution of the pyrene luminescent chromophore to form a dispersion of the silicon nanocrystal in the solution of the pyrene luminescent chromophore, and
heating the dispersion of the silicon nanocrystal in the solution of the pyrene luminescent chromophore.

24. The method of claim 23, further comprising dispersing the silicon nanocrystal in a solution of a linking agent, wherein the linking agent comprises a moiety reactive with the silicon nanocrystal.

25. The method of claim 24, wherein the moiety of the linking agent reactive with the silicon nanocrystal includes an alkenyl group.

26. The method of claim 24, wherein the linking agent is a C1-C50 alkyl, alkenyl, or alkynyl.

27. The method of claim 24, wherein linking agent is a C1-C8 alkyl group.

28. The method of claim 24, wherein linking agent is a C8-C20 alkyl group.

29. The method of claim 24, wherein the pyrene luminescent chromophore and the linking agent are in a ratio 1:1 to 1:50.

30. A method of increasing photoluminescence quantum yield of a silicon nanocrystal, the method comprising the steps of:
providing a silicon nanocrystal, and
treating the silicon nanocrystal with a molar excess of a pyrene luminescent chromophore configured to covalently bind to the silicon nanocrystal, thereby forming the photoactive particle of claim 1.

31. The method of claim 30, further comprising exposing the photoactive particle to electromagnetic radiation having the first wavelength.

32. The method of claim 30, wherein the silicon nanocrystal is from 1 to 10 nm in diameter.

33. The method of claim 30, wherein the photoactive particle exhibits a greater intensity of brightness than the silicon nanocrystal before treating.

34. The method of claim 30, wherein the photoactive particle exhibits a brightness increase of about 300% more than the silicon nanocrystal before treating.

35. The method of claim 30, wherein the photoactive particle exhibits a photoluminescence quantum yield at least double that of the silicon nanocrystal before treating.

* * * * *